United States Patent [19]

Diamandis

[11] Patent Number: 5,723,302
[45] Date of Patent: Mar. 3, 1998

[54] DETECTION OF PROSTATE-SPECIFIC ANTIGEN IN BREAST TUMORS

[75] Inventor: Eleftherios Diamandis, Toronto, Canada

[73] Assignee: Nordion International Inc., Canada

[21] Appl. No.: 607,777

[22] Filed: Feb. 27, 1996

Related U.S. Application Data

[63] Continuation-in-part of Ser. No. 532,808, Jan. 5, 1996.

[30] Foreign Application Priority Data

May 14, 1993 [GB] United Kingdom .................. 9309966

[51] Int. Cl.$^6$ .................... G01N 33/53; G01N 33/574; G01N 33/48
[52] U.S. Cl. .................... 435/7.1; 435/7.23; 435/7.72; 436/63; 436/64
[58] Field of Search .................. 435/7.1, 7.23, 435/7.72; 436/63, 64

[56] References Cited

PUBLICATIONS

Giai, M. et al, "Prostate–specific antigen in serum of women with breast cancer" Br. J. Cancer, vol. 72, pp. 728–731, 1995.

Diamandis, E.P. et al, "Detection of prostate–specific antigen immunoreactivity in breast tumors" Breast Cancer Res. and Treat. vol. 32, pp. 301–310, 1994.

Levesque, M. et al, "Prostate–specific antigen expression by various tumors" J. Clin. Lab. vol. 9, pp.123–128, 1995.

Papotti, M. et al, "Immunocytochemical detection of prostate–specific antigen (PSA) in skin adnexal and breast tissues and tumors" Bas Appl. Histochem vol. 33, pp. 25–29, 1989.

Yu, H. et al, "Immunoreactive prostate–specific antigen levels in female and male breast tumors and its association with steroid horomone receptors and patient age" Clin. Biochem. vol. 27, pp.75–79, 1994.

"Endocrinology prostate–specific antigen, not just a guy thing" Cancer Biotech. Weekly, Feb 20, 1995.

Acta Cytologica, vol. 33, No. 6, 1989 F.C. Schmitt, et al., pp. 899–902, "Cytology and Immunocytochemistry of Bilateral Breast Metastases from Prostratic Cancer".

Clinical Biochemistry, vol. 21, No. 3, Jun. 1988, pp. 139–150, Diamandis, E.P., "Immunoassays with Time–Resolved Fluorescence Spectroscopy:Principles and Applications".

Bas. App. Histochem., vol. 33, 1989, pp. 25–29, M. Papotti et al., "Immunocytochemical Detection of Prostate–Specific Antigen (PSA) in Skin Adnexal and Breast Tissues and Tumors".

Eur. J. Clin. Chem. Clin. Biochem. vol. 29, 1991, pp. 787–794, W.G. Wood et al., "The Establishment and Evaluation of Luminescent–Labelled Immunometric Assays for Prostate–Specific Antigen–alpha1–Antichymotrypsin Complexes in Serum".

Clinical Chemistry, vol. 39, No. 10, 1993, pp. 2108–2114, H. Yu et al., "Ultrasensitive Time–Resolved Immunofluorometric Assay of Prostate–Specific Antigen in Serum and Preliminary Clinical Studies".

*Primary Examiner*—Toni R. Scheiner
*Assistant Examiner*—Yvonne Eyler
*Attorney, Agent, or Firm*—Banner & Witcoff, Ltd.

[57] ABSTRACT

This invention relates to the detection of prostate-specific antigen (PSA) subfractions in serum as a prognostic or predictive indicator for breast carcinoma. In particular this invention relates to an in vitro blood test for the diagnosis of breast cancer using serum PSA subfractions. Serum PSA subfractions are remarkably different in the serum from breast cancer patients, normal male patients and female patients treated for breast cancer.

11 Claims, 14 Drawing Sheets

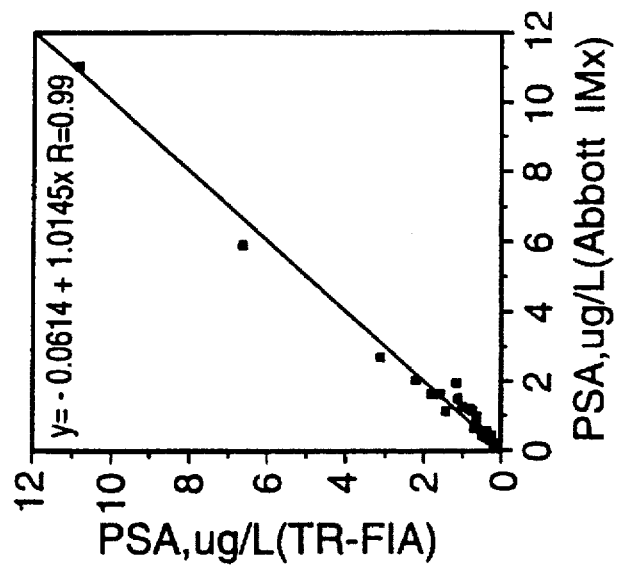
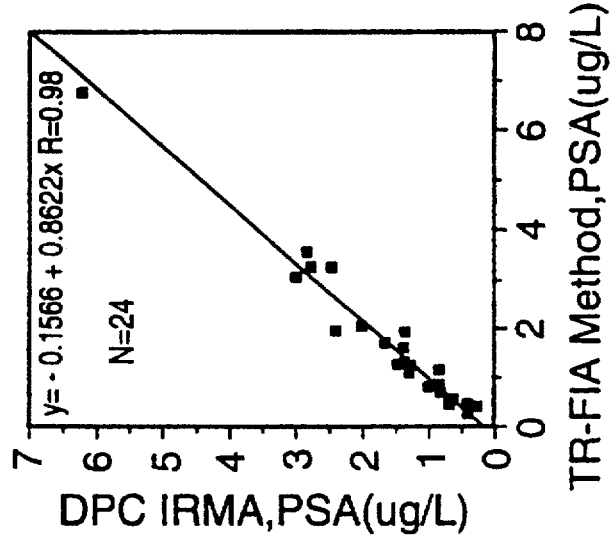
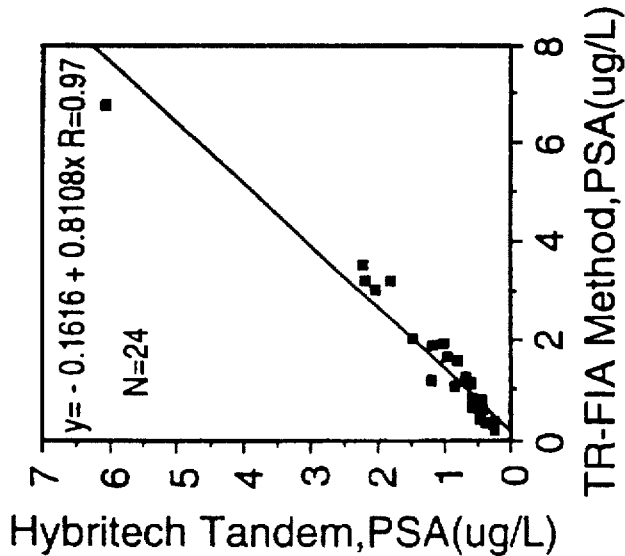
FIG.1C
FIG.1B
FIG.1A

DETECTION OF PROSTATE-SPECIFIC ANTIGEN IN BREAST TUMORS

RELATED APPLICATIONS

This application is a continuation in part of U.S. Ser. No. 08/532,808 filed Jan. 5, 1996, which is a 371 of PCT application CA 94/00267 filed May 13, 1994.

FIELD OF THE INVENTION

This invention relates to a method for the diagnosis of breast cancer using serum PSA subfractions. PSA serum subfractions are remarkably different in breast cancer patients as compared with male patients, normal females and females treated for breast cancer.

BACKGROUND OF THE INVENTION

Considerable research and related diagnosis has been undertaken in this field of healthcare. In order to facilitate reference to prior art developments and procedures, journal articles are listed at the end of this specification and are hereinafter referenced by number.

Breast cancer is a leading cause of mortality and morbidity among women (1-4). One of the priorities in breast cancer research is the discovery of new biochemical markers which could be used for diagnosis, prognosis and monitoring (4, 5). Breast cancer is one of a few cancers that is dependent on steroid hormones and their receptors. Currently, estrogen and progesterone receptor analysis is performed routinely as an aid in prognosis and selection of therapy (4-6).

Current indicators for monitoring breast tumors include: tumor size, estrogen receptors, progesterone receptors, age, aneuploidy, mitotic activity and Ki67 (29). The prognostic usefulness of these factors depends on their ability to evaluate which patients with breast cancer require aggressive adjuvant therapeutic treatment post surgery and which patients should be monitored.

Mutation of the p53 tumor suppressor gene is one of the most commonly known genetic defects in human cancer, including breast cancer and results in mutant protein accumulating to high concentrations. Overexpression of p53 protein has been found to be an independent predictor of early disease recurrence (29). The accumulation of p53 protein has been found to be an independent marker of shortened survival (30). The majority of tumors that do not produce mutant p53 protein are estrogen and/or progesterone receptor-positive (14).

Prostate cancer is a leading cause of mortality and morbidity among men (7, 8). Prostate tissue and cancer is also dependent on steroid hormones and therapy that takes advantage of this is currently routinely used (9-10). One of the hallmarks of prostate cancer is the appearance in serum, at elevated concentrations, of a 30-33-KDa glycoprotein, prostate specific antigen (PSA) (11). PSA is a serine protease found at high levels in seminal fluid and prostate epithelial cells (38). PSA production in the prostate is regulated by androgenic steroids, which bind to androgen receptors and up-regulate transcription of the PSA gene (11, 38).

Currently PSA is a highly valuable marker for prostate cancer screening diagnosis, and post-surgical monitoring of prostate cancer patients, as well as for the detection of micrometastases (38). Normal male serum PSA levels are usually below 4 µg/L (11,38) and it is detectable in two molecular forms for both normal and prostate cancer subjects; as free PSA or as complexed with a proteinase inhibitor, ACT ($\alpha_1$-antichymotrypsin).

Previous immunohistochemical studies found no PSA immunoreactivity in breast or other tumors (17) or found occasional PSA immunoreactivity with polyclonal but not monoclonal antibodies, suggesting cross-reactivity effects (18). We have now discovered the presence of PSA in breast tumors. Prior studies have also shown that PSA is undetectable in the serum of most women. A few women do have traces of serum PSA which are thought to be produced in the periurethral glands. In a recent study involving 1161 normal female sera we have reported that <5% of the samples had PSA concentrations >50 ng/L (50). A recent report studying associations between total serum PSA levels from normal women, women with breast cancer and breast tumor PSA levels, indicated that there was no diagnostic or monitoring value of female serum total PSA (52). We have found that PSA is present in two subfractions in female serum. We have now discovered that the differences in serum PSA subfractions between breast cancer patients and normal women can be used to diagnose breast cancer.

SUMMARY OF THE INVENTION

We have discovered that serum PSA subfractions can be correlated with the presence of breast cancers in females. This allows for a new non-invasive method for the diagnosis of breast cancer which comprises a simple blood test to determine serum PSA subfractions for quantitation and evaluation.

According to an aspect of the present invention is an in vitro biological assay for the detection of free PSA in female serum indicating the presence or absence of breast cancer.

According to another aspect of the invention is an in vitro biological assay for the diagnosis of breast cancer in a patient comprising the determination of the relative mounts of free PSA and PSA-ACT complexes which are indicative of the presence or absence of breast cancer.

According to an aspect of the invention is an in vitro method for the diagnosis of breast cancer comprising i) performing a highly sensitive separation technique on a serum sample to establish PSA subfractions; and ii) performing a highly sensitive assay on the PSA subfractions which is capable of detecting at least 1 ng/L of PSA to determine the predominant molecular form of PSA; and iii) determining the mount of PSA-ACT complex compared to free PSA to indicate the presence or absence of breast cancer.

According to another aspect of the present invention is an in vitro method for the diagnosis of an endocrine cancer in a patient comprising, i) performing a highly sensitive separation technique on a serum sample to establish PSA subfractions; and ii) performing a highly sensitive assay on the PSA subfractions which is capable of detecting at least 1 ng/L of PSA to determine the predominant molecular form of PSA; and iii) determining the mount of PSA-ACT complex compared to free PSA to indicate the presence or absence of breast cancer.

BRIEF DESCRIPTION OF THE DRAWINGS

Preferred embodiments of the invention are demonstrated with respect to the drawings wherein:

FIG. 1A. Analysis of PSA in breast tumor extracts by a TR-FIA method. Comparison of TR-FIA with the Hybritech Tandem® PSA kit for 24 breast tumor extracts with PSA >0.3 µg/L.

FIG. 1B. Analysis of PSA in breast tumor extracts by DPC IRMA-Count® PSA kit. Comparison of TR-FIA with the DPC IRMA-Count® PSA kit for the same extracts as in FIG. 1A.

FIG. 1C. Analysis of PSA in breast tumor extracts by Abbott IM$_x$® assay. Comparision of TR-FIA with the Abbott IM$_x$® assay. The equation represents linear regression analysis and R is the correlation coefficient. One tumor extract sample, not included in the graph, had a PSA value of 61.4 µg/L, by TR-FIA, 39.4 µg/L by Hybritech and 51.8 µg/L by the DPC kit (not measured by IM$_x$. These data confirm the presence of PSA in breast tumor extracts by three different immunological techniques.

DETAILED DESCRIPTION OF THE PREFERRED EMBODIMENTS

PSA in Breast Tumour Extracts

Figure 2A:
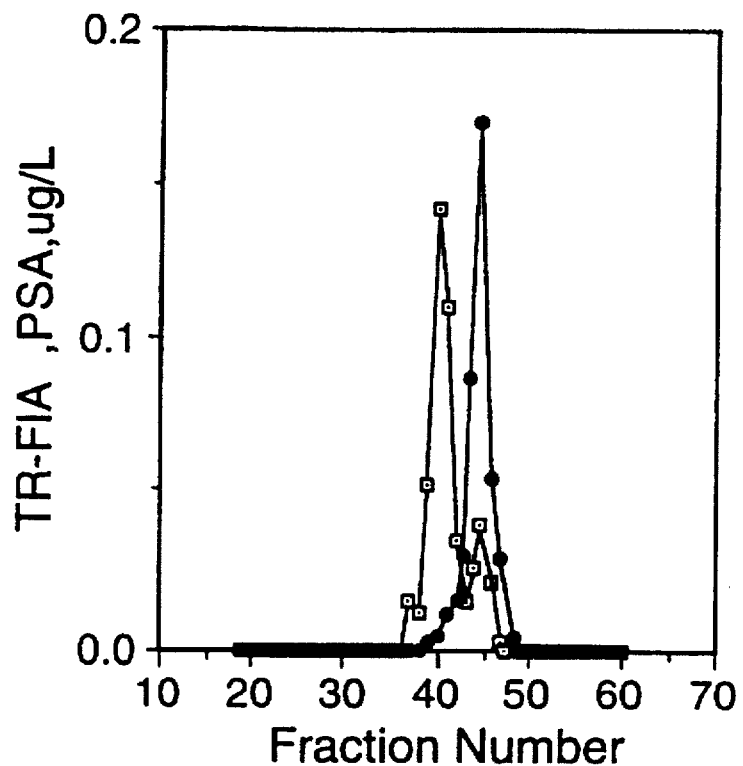
FIG. 2A. Analysis of PSA by TR-FIA in high performance liquid chromatographic (HPLC) fractions. The column was calibrated with a molecular weight standard solution containing thyroglobulin (670 KDa), IgG (158 KDa), ovalbumin (44 KDa), myoglobin (17 KDa) and cyanocobalamin (1.4 KDa). Breast tumor extract with PSA of 6.7 µg/L by TR-FIA and a male serum sample with 4.27 µg/L of PSA, by TR-FIA. PSA-ACT in male serum is the predominant form; in the breast tumor extract, PSA is in the free form.

We have carried out extensive investigations on breast tumors and surprisingly, found that twenty-nine percent of the breast tumor extracts were found positive for PSA (cutoff level 0.05 µg/L or 0.03 ng/mg total protein). PSA was associated with tumors that were estrogen and/or progesterone receptor-positive (P<0.002). No association was found between PSA levels and levels of the p53 tumor suppressor gene product (P=0.37). High performance liquid chromatography revealed that PSA is present in the tumor predominantly in its free, 30–33 KDa form. PSA-positive tumors were associated with younger (premenopausal) women (P=0.012) and earlier disease stage (P=0.064). It appears that PSA production is induced by steroid hormone receptor-ligand complexes.

The cutoff value of 0.05 µg/L (0.03 ng/mg total protein) for PSA in the breast cytosols was arbitrarily selected based on the PSA assay sensitivity. PSA values >0.05 µg/L can be easily and precisely quantified by using the developed assay of the invention. It is appreciated that various assay techniques may be used to detect PSA; for example, enzyme immunoassay, radioimmunoassay, chemi- or bioluminescent immunoassay, fluorescent immunoassay and DNA-based assays to detect expression of the PSA gene at the mRNA level.

In accordance with a preferred aspect of the invention, an assay comprising an ultrasensitive detection method for prostate-specific antigen in breast tumor extract involving time-resolved fluoroimmunoassay is provided. Breast tumor extract is incubated with monoclonal anti-PSA antibody. Biotinylated polyclonal or monoclonal antibody specific to PSA is added to bind to any bound PSA. Alkaline phosphatase-labelled streptavidin (SA-ALP) is added. The activity of ALP is measured by adding the substrate 5-fluorosalicyl-phosphate and then adding $Tb^{3+}$-EDTA to form a fluorescent chelate. Fluorescence is measured over time to indicate the presence of PSA. The presence or absence of PSA can be used as a prognostic and predictive indicator of breast carcinoma. The invention's detection method can also be used for detecting the presence of other markers or substances, such as p53 protein, using the appropriate antibody.

The data we have established and as summarized in Table I, establishes an association between breast tumors and tissue level of PSA. 525 breast tumor extracts were analyzed for PSA with the results as shown in Table I. From these tumor extracts, 374 (71.2%) had PSA levels <0.05 µg/L and were considered negative for PSA. One hundred and fifty-one (28.8%) of the tumor extracts had PSA levels >0.05 µg/L, 96 (18.3%) had PSA levels >0.1 µg/L and 49 (9.3%) had PSA levels >0.3 µg/L. Samples with a PSA concentration of >0.3 µg/L, which is potentially measurable by commercial kits, were also analyzed by the Hybritech Tandem® M-R PSA kit, by the IRMA-Count® PSA kit and by the Abbott $IM_x$ Kit. The results are shown in FIG. 1.

To further exclude the possibility of non-specific effects, the assay was repeated for 25 highly positive samples (PSA >0.3 µg/L) under the following conditions: (a) the assay was run in the absence of capture mouse monoclonal anti-PSA antibody (b) the assay was run by using an irrelevant capture mouse monoclonal antibody (against alpha-fetoprotein) (c) the assay was run after substitution of the polyclonal rabbit detection antibody with biotinylated rabbit IgG. In all cases, background signals were obtained verifying that non-specific effects were absent.

Figure 2B:
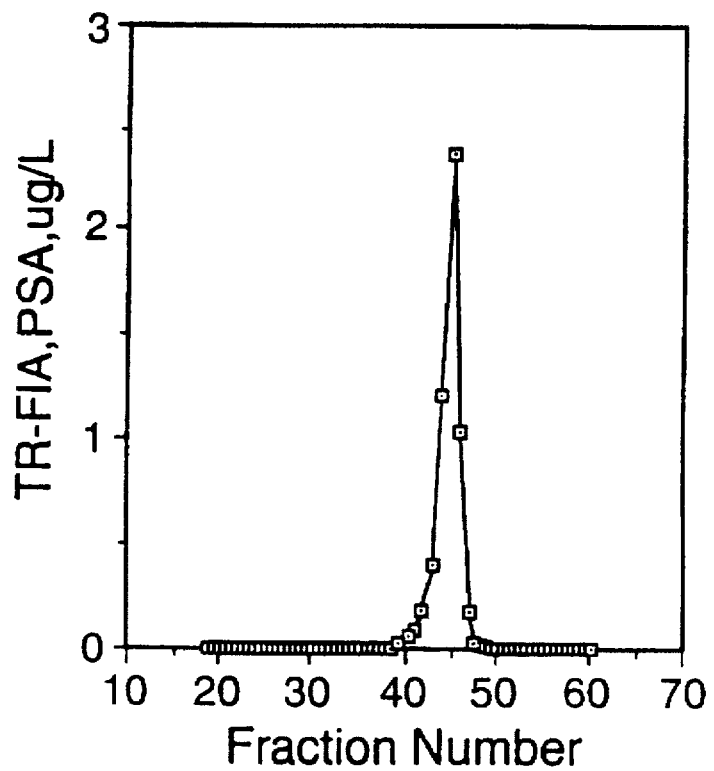
FIG. 2B. Analysis of PSA by TR-FIA in high performance liquid chromatographic (HPLC) fractions. The column was calibrated with a molecular weight standard solution coming thyroglobulin (670 KD), IgG (158 KD), ovalbumin (44 KD), myoglobin (17 KD) and cyanocobalamin (1.4 KD). Breast tumor extract with PSA of 61.4 µg/L by TR-FIA. The peak at fraction 45 corresponds to a molecular weight of approximately 30 KDa and represents free PSA. The peak at fraction 40 corresponds to a molecular weight of approximately 100 KDa and represents PSA bound to $\alpha_1$-antichymotrypsin.

PSA immunoreactivity was further investigated in two breast tumor extracts by using high performance liquid chromatography (HPLC). One male serum sample with a PSA concentration of 4.27 µg/L by TR-FIA and one negative breast tumor extract were used as positive and negative controls. Analysis of PSA was performed in the HPLC fractions and the results are shown in FIG. 2. The PSA-negative breast tumor extract, run between the positive samples, gave undetectable readings in all fractions, in all cases. The PSA immunoreactivity in the two breast tumor extracts, elutes as a single peak at fraction 45 and corresponds to a molecular weight of approximately 30-33 KDa. The PSA immunoreactivity in the male serum sample elutes in two peaks at fractions 40 and 45 and corresponds to molecular weights of approximately 100 KDa and 30-33 KDa, respectively. These two peaks correspond to PSA bound to $\alpha_1$-antichymotrypsin and to free PSA, respectively (13, 15, 16). These findings demonstrate that the PSA in the breast tumor extracts is present exclusively in the free 30-33 KDa form.

In order to exclude the possibility of contamination of the extracts, six PSA-positive and six PSA-negative breast tumors that were stored frozen at -70° C. were reextracted. Rerun of the fresh extracts with the TR-FIA assay confirmed the original results in all cases. Ninety-four breast tumor extracts were also obtained from another steroid hormone receptor laboratory serving different hospitals in Toronto. From these, 17 (18%), 12 (13%) and 5 (5.3%) had PSA values >0.05, >0.1 and >0.3 µg/L, respectively.

Recovery experiments done by spiking PSA-negative tumor extracts with seminal plasma PSA gave values averaging 83% of the amount of exogenous PSA added. Dilution experiments were performed by diluting a breast tumor extract with a high PSA concentration (20.4 µg/L) with either a 6% (w/v) bovine serum albumin solution or a PSA-negative breast tumor extract. The obtained values, at dilutions ranging from 2 to 32-fold, were very close to those predicted by the PSA-value in the undiluted specimen (100±5%). A batch of 16 breast tumor extracts (four with PSA <0.05 µg/L and twelve with PSA >1 µg/L) were also sent to two different laboratories performing routine PSA assays by the Hybritech and DPC methods. In both cases, their values were very similar to the ones obtained by our method. These data further demonstrate that the invention's PSA detection results are not due to any non-specific effects and that contamination is very unlikely.

Although we describe detection of PSA with a time-resolved immunofluorometric technique, it is understood that those skilled in the art may use other techniques presently available or future immunological techiques for PSA quantification to at least 0.03 ng/mg of total protein. For example, techniques capable of such sensitivity include chemiluminescence with acridinium esters as labels, enzymatically triggered chemiluminescence with alkaline phosphatase and dioxetanes substrates luminol chemiluminescence enhanced by horseradish peroxidase, immunoassays using alkaline phosphatase and the fluorogenic substrate 4-methylumbelliferyl phosphate or p-nitrophenyl phosphate, immunoassay using horseradish peroxidase and substrates like ABTS and tetramethylbenzidine, time-resolved immunofluorometric assays with $Eu^{3+}$ as label and methods based on electroluminescence.

In addition, PSA expression may also be detected by determining whether mRNA for PSA is present in a breast tumor sample. The preferred procedure for detecting mRNA for PSA is by PCR amplification. Total RNA or mRNA is isolated from breast tumor samples and cDNA synthesized by reverse transcription. PCR amplification of cDNA is accomplished using PSA specific primers. A probe is used to detect cDNA for PSA. Other methods for detecting an RNA for PSA may also be used, such as, the Northern Blot technique.

For most of the tumor extract samples analyzed for PSA, data for estrogen (ER) and progesterone (PR) receptor concentrations was available. Also 474 samples were analyzed for the presence of the p53 tumor suppressor gene product, using a method previously described (14). Tumors were then classified as being positive or negative for ER, PR, p53 and PSA using the following negativity cutoff levels: <10 fmol/mg of total protein for ER and PR (14, 30,31); <3 U/L, for p53 (equivalent to 0.02 ng/mL) (14) and <0.05 µg/L for PSA. The data are summarized in Table II.

There is a significant association between the presence of estrogen and/or progesterone receptors and the presence of PSA in the tumors (P<0.002). PSA is independently associated with ER and PR because minors which are either ER(+) only or PR(+) only still have higher percentage of positivity for PSA in comparison to minors which are negative for both receptors. Additionally, the highest percentage of PSA-positive tumors is associated with tumors that are positive for both the ER and PR (Table II). There is no association between the presence of PSA and the presence of the p53 tumor suppressor gene product (P=0.37). It has recently been shown that the latter is strongly associated with estrogen and/or progesterone receptor-negative tumors (14) an association also shown in Table II for the samples of this study Correlation studies using linear regression analysis between ER and PR and PSA, for all samples of this study (N=525) gave the following Pearson correlation coefficients: r=−0.023, not significantly different from zero (NS), P=0.60 for ER and r=−0.015, (NS), P=0.71 for PR When only the PSA-positive tumors were used for correlation (N=151) the following Pearson correlation coefficients were obtained: r=−0.015, (NS), P=0.85 for ER and r=−0.068, (NS), P=0.40 for PR.

Some breast tumors had very high PSA levels. Highest values were obtained for five tumors in which PSA levels were >20 µg/L in the extracts and between 200–1000 ng of PSA per g of breast tumor tissue.

Figure 3:
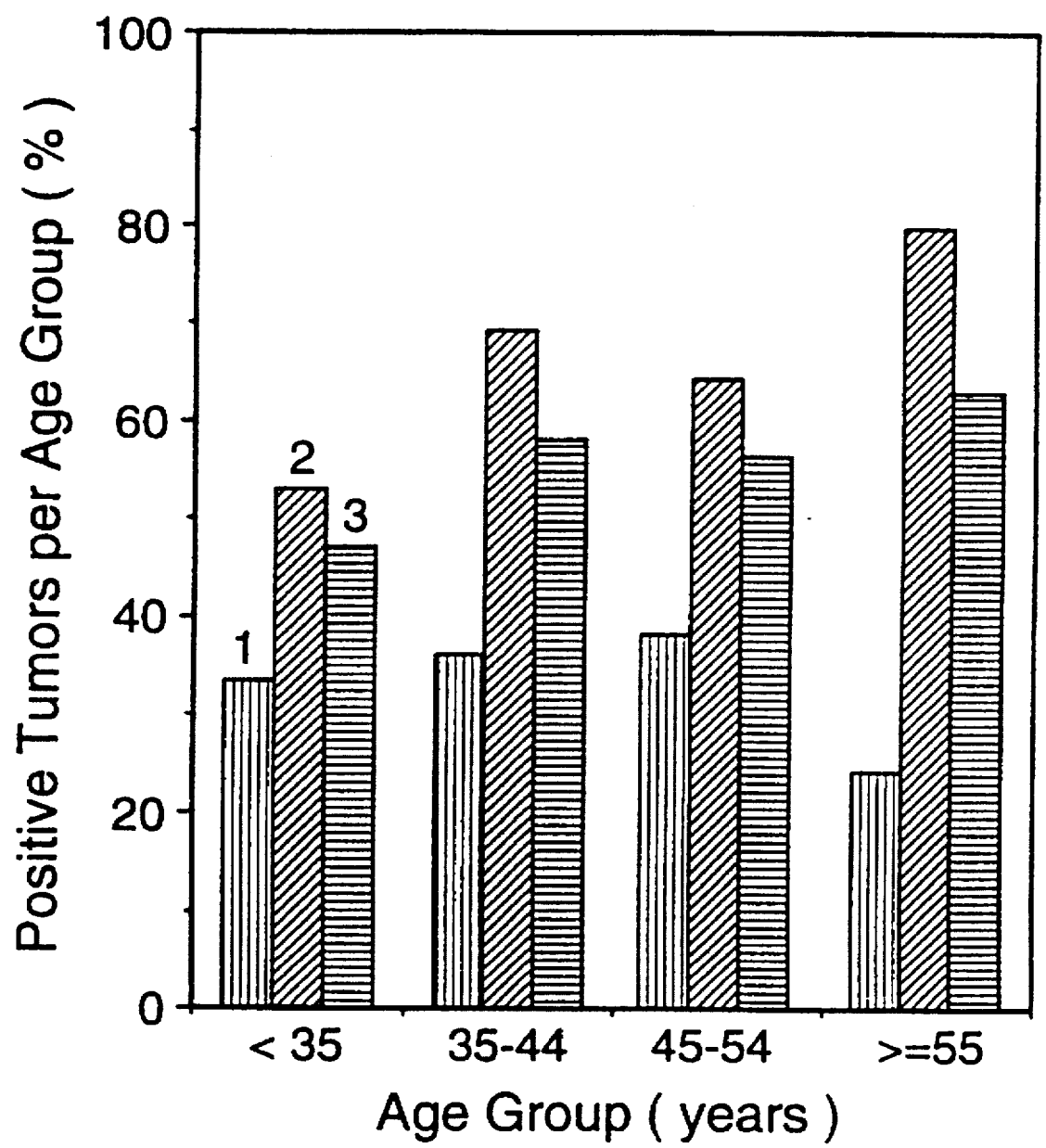
FIG. 3. Percentage of PSA-positive (1), estrogen receptor-positive (2) and progesterone receptor-positive (3) tumors in four groups of patients with age (years) of <35, 35–44, 45–54 and greater or equal to 55. PSA-positive tumors were preferentially distributed among younger patients (P=0.012) and estrogen receptor-positive tumors among older patients (P=0.001). The progesterone receptor-positive minors were not preferentially distributed in any age group (P=0.45).

Association analysis between PSA presence in breast tumors and patient age gave the results shown in Table III and FIG. 3. PSA was distributed preferentially in younger (premenopausal) patients and this preference was statistically significant (P=0.012).

Figure 4:
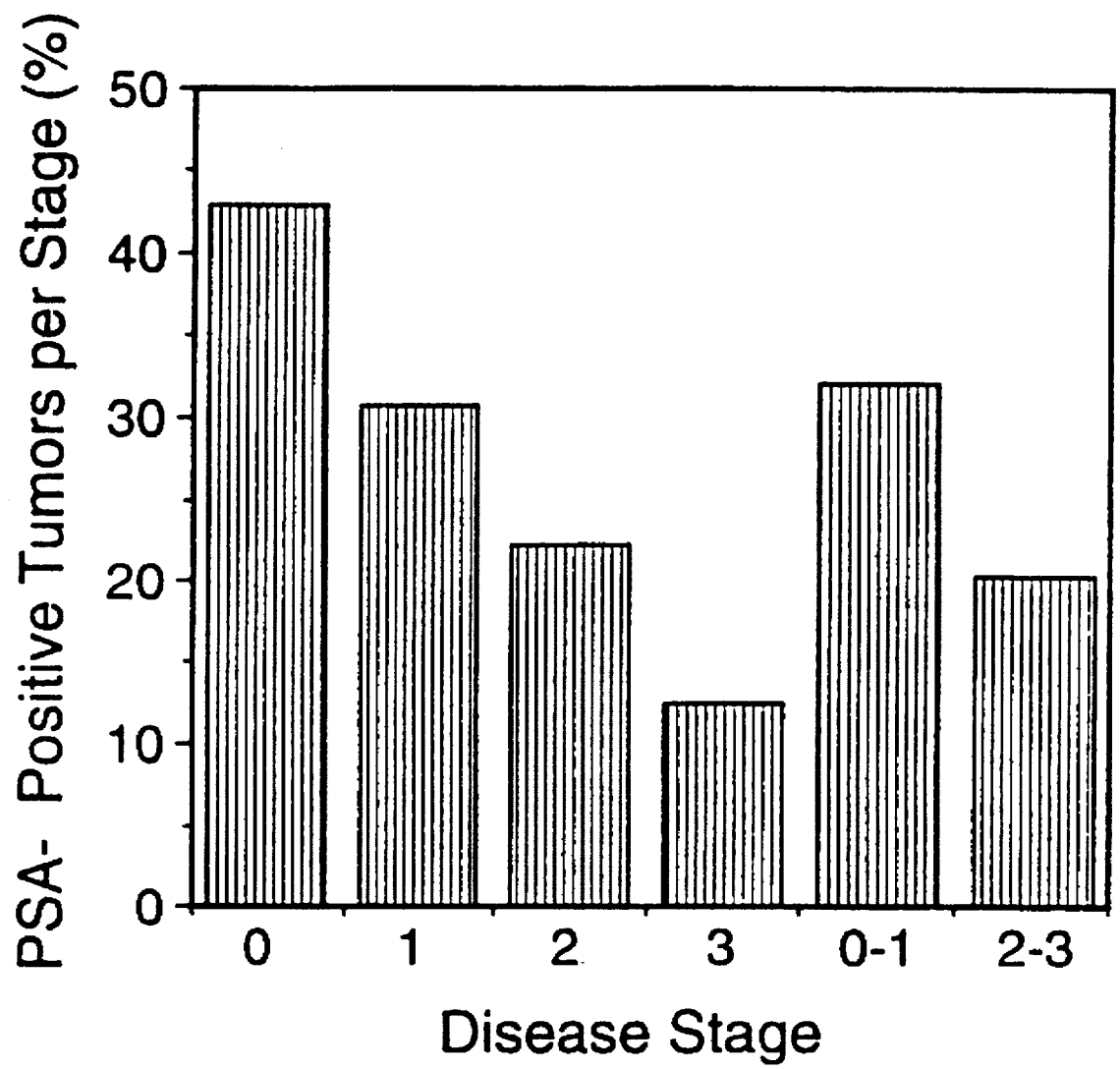
FIG. 4. Percentage of PSA-positive tumors in each disease stage or in stages 0–1 or 2–3. Stages 0–1 indicate a localized tumor and stages 2–3 indicate increased spreading of the tumor. There is a clear trend for PSA-positive tumors to be associated with lower disease stage (see also Table 4).

Tumor stage was available in 203 patients. The results of the distribution of PSA-positive tumors in various stages is given in Table IV and FIG. 4. Clearly, there is a trend for the PSA-positive tumors to be preferentially associated with lower disease stage.

PSA-positive tumors are predominantly ER(+) and PR (+). The presence of PSA in a tumor is indicative of functional ER and PR because PSA is closely associated with the PR (Table V). PR is a product of the action of the ER and is indicative of functional ER. Thus, monitoring PSA would be a useful test to identify patients who possess functional ER and PR. These patients are the ones most likely to respond to endocrine treatment which currently consists of administering one or more of the following: Antiestrogens, antiprogestins, antiandrogens, progestins, androgens, glucocorticoids. Thus, the classification of patients as PSA(+) and PSA(−) may be useful to select those who will benefit from endocrine treatment.

In addition, a subgroup of PSA-positive and ER-negative patients was suprisingly found to have a good prognosis and respond well to endocrine treatment. In order to examine the prognostic significance of PSA in the subsets of patients who are ER-negative or ER-positive, the hazard ratio between PSA-positive and PSA-negative patients was calculated for two subsets being the ER-negative and the ER-positive groups, using the Cox regression model. The analysis was done at two cut-off levels of the receptors, 10 fmol/mg or 20 fmol/mg since with the receptor assays used, levels between 10–20 fmol/mg are considered equivocal. The results of the analysis are shown in Table 6. In the ER-positive group the risks of relapse were almost identical between PSA-positive and PSA-negative patients, which was expected since it is known that steroid hormone receptors are favourable prognostic indicators in breast cancer. However, in the ER-negative group, the risk of relapse was substantially reduced when the tumors were PSA-positive (hazards ratio 0.13–0.20). The difference was statistically significant when the cutoff level of the receptors was 20 fmol/mg due to the increase in the number of patients in this subgroup. The hazards ratio in the ER-negative subgroup remained very low even when nodal status, clinical stage and histological type were controlled in the analysis.

Figure 6A:
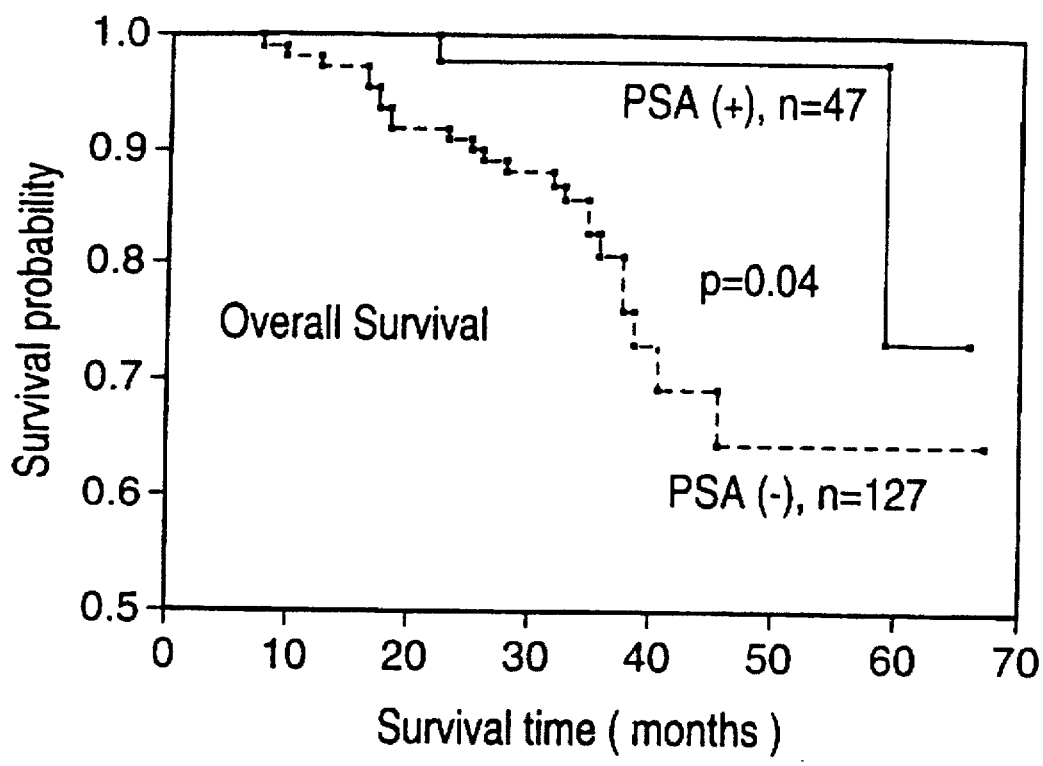
FIG. 6A. Kaplan Meier Survival curve for PSA-positive and PSA-negative patients showing overall survival.
Figure 6B:
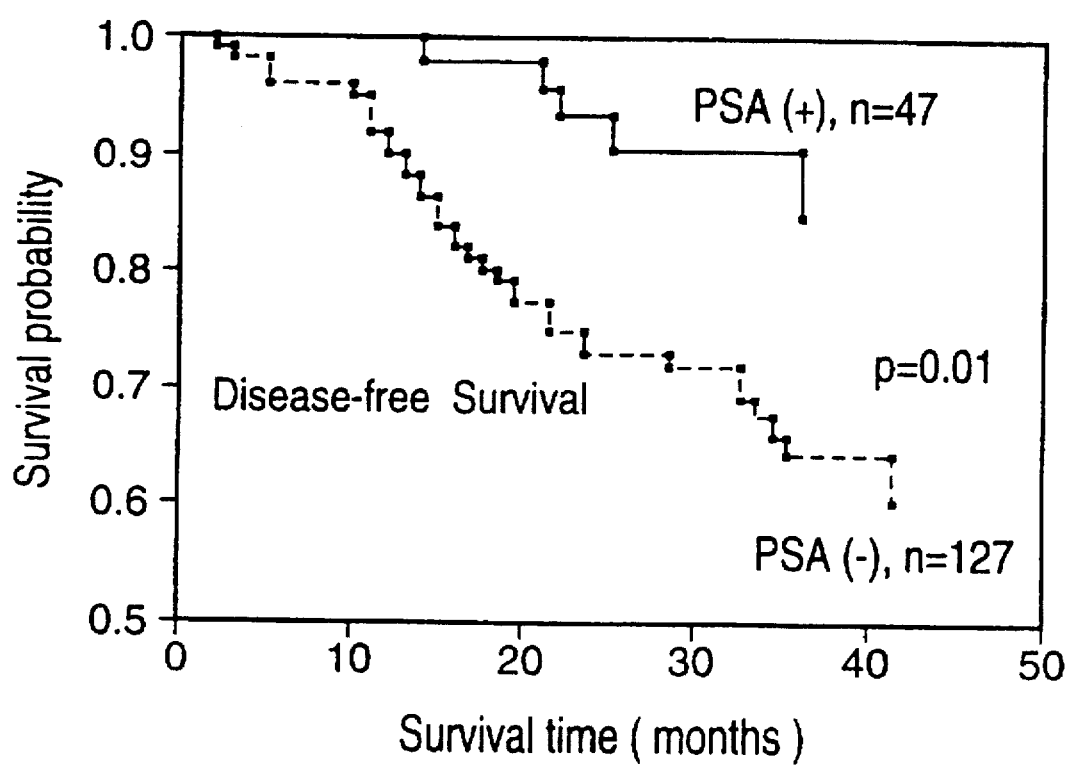
FIG. 6B. Kaplan Meier Survival curve for PSA-positive and PSA-negative patients showing disease-free survival.
Figure 7A:
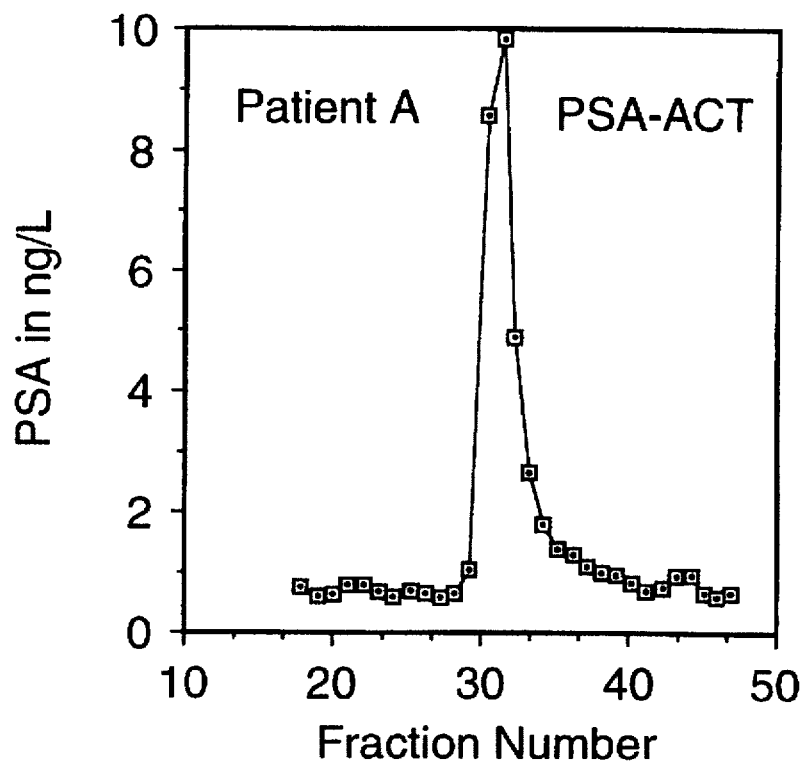
FIG. 7. Separation of total serum PSA in six different patients by high-performance liquid chromatography and assay of the fractions by a highly sensitive time-resolved immunofluorometric methodology. Patients are described in Table 7. The PSA-$\alpha_1$-antichymotrypsin complex (PSA-ACT) elutes at fraction 30±1 (molecular weight of ~100 KDa). Free PSA (F-PSA) elutes at fraction 39±1 (molecular weight of ~33 KDa). PSA is circulating as a complexed form (PSA-ACT) in the serum of normal women (A, B, C), while the major molecular form in the serum of breast cancer women is F-PSA (D, E, F).
Figure 7B:
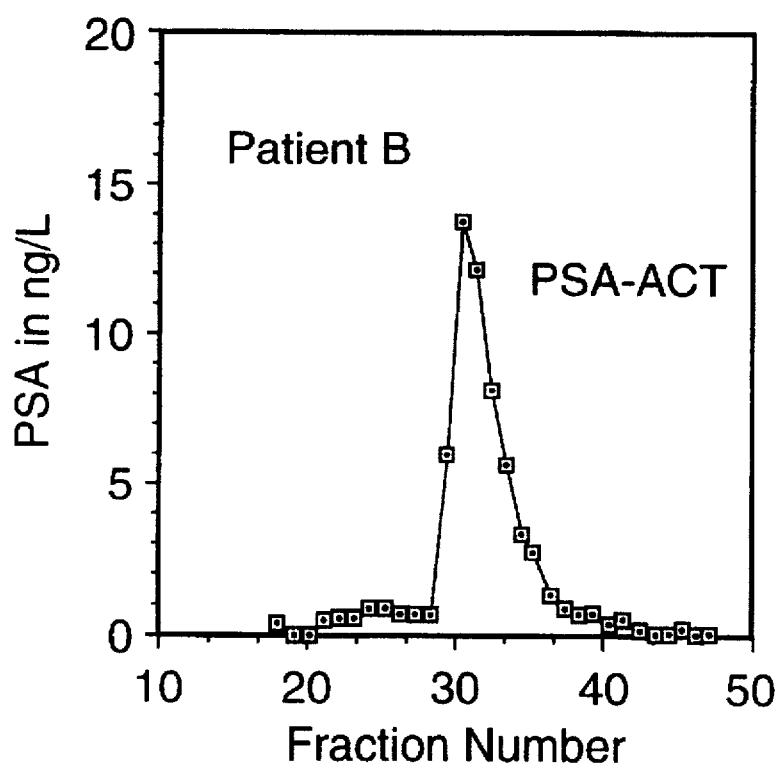
Figure 7C:
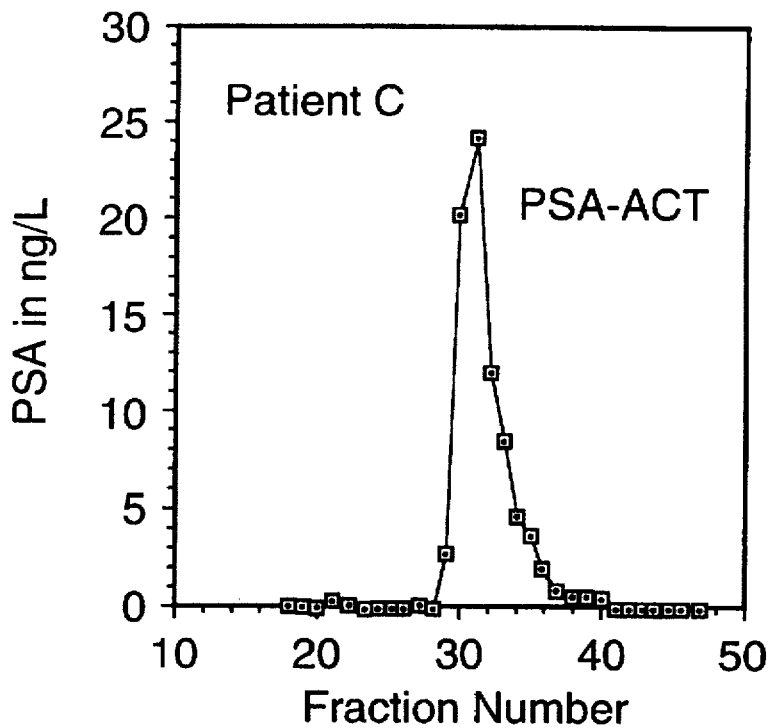
Figure 7D:
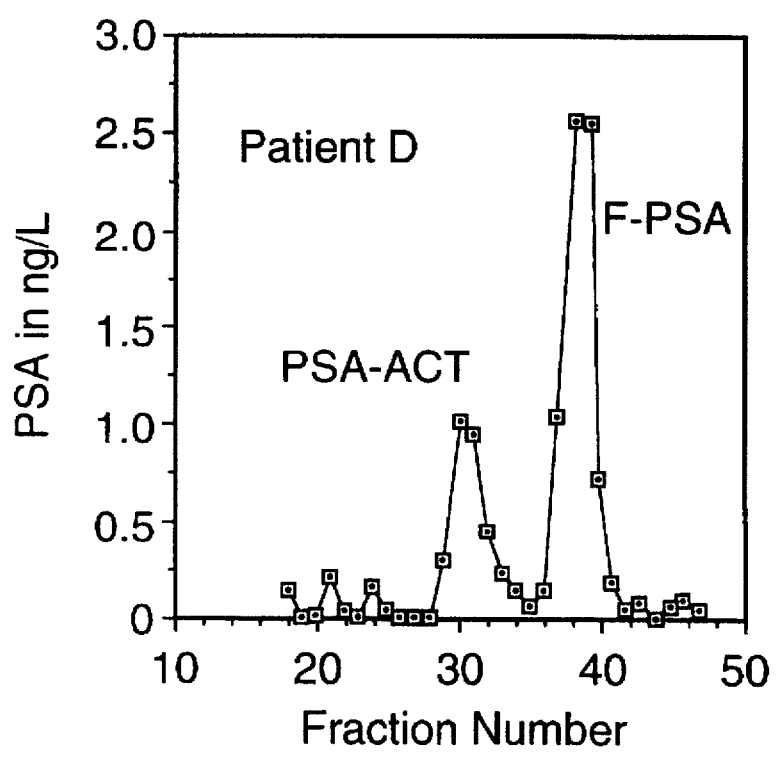
Figure 7E:
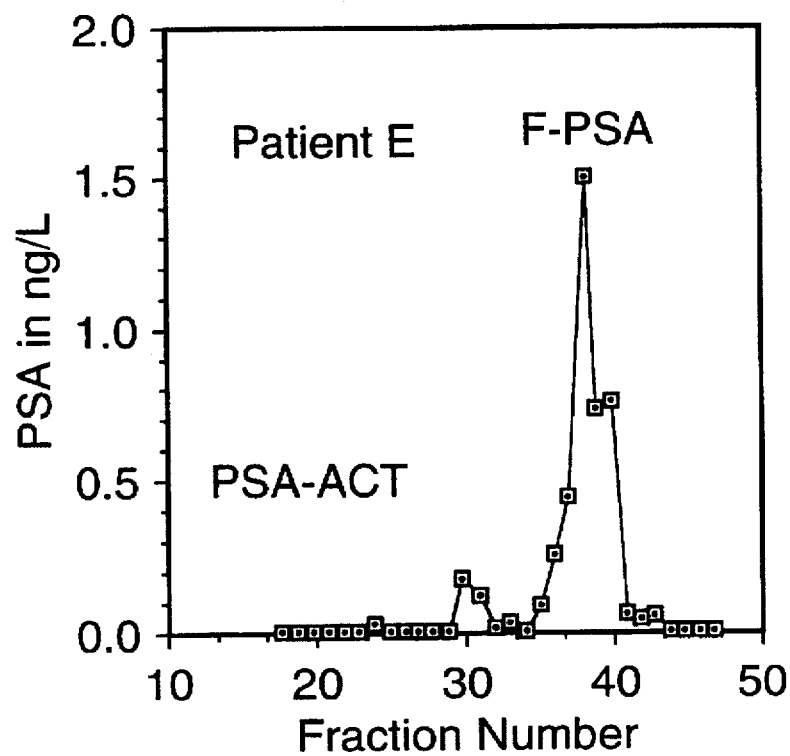
Figure 7F:
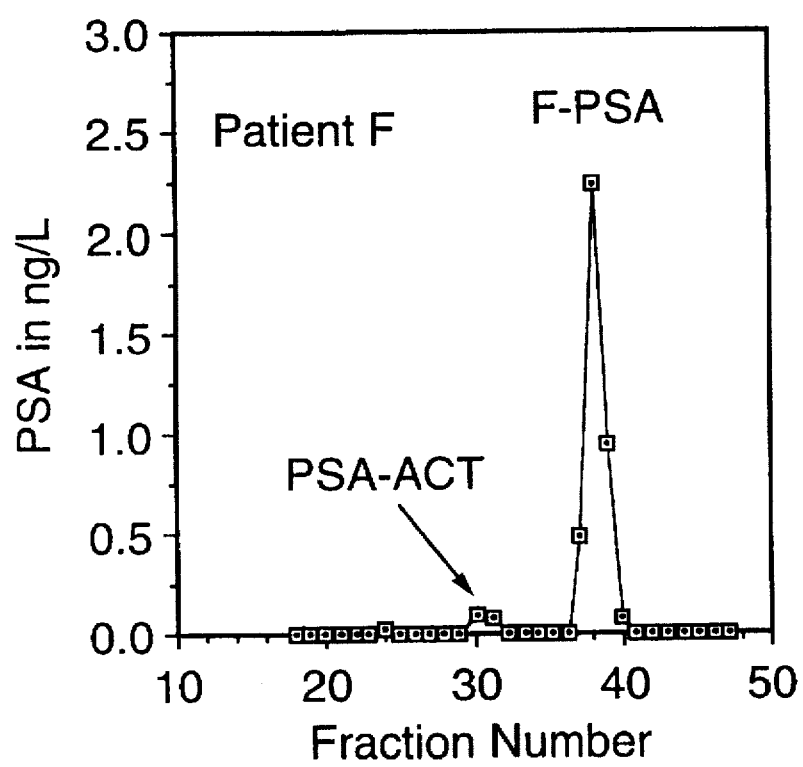
Figure 8A:
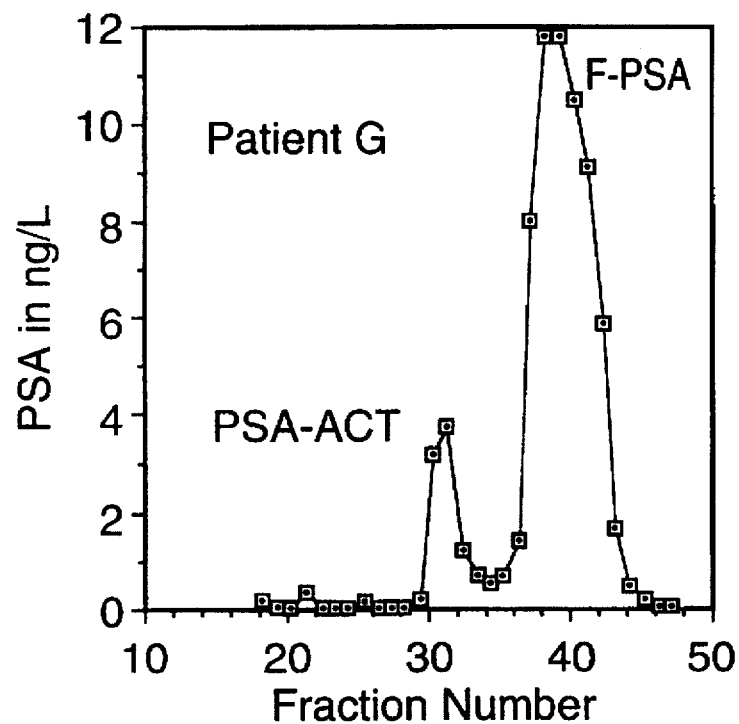
FIG. 8. Separation of total serum PSA in an additional six patients by high-performance liquid chromatography and assay of the fractions with a highly sensitive time-resolved immunofluorometric methodology. Patients are described in Table 7. The data represent serum fractions of post-operative female patients with primary breast cancer. PSA-ACT elutes at fraction 305 (molecular weight of ~100 KDa). Free PSA (F-PSA) elutes at fraction 39±1 (molecular weight of ~33 KDa). PSA is circulating primarily as a complexed form (PSA-ACT) in six out of seven post-surgical sera of breast cancer women (one serum with 100% PSA-ACT is not shown). The minor molecular form of PSA in some post-operative sera is F-PSA. In patient G (for which no current clinical status of the disease was available) the primary molecular form is the F-PSA; we suspect that this case represents breast cancer relapse.
Figure 8B:
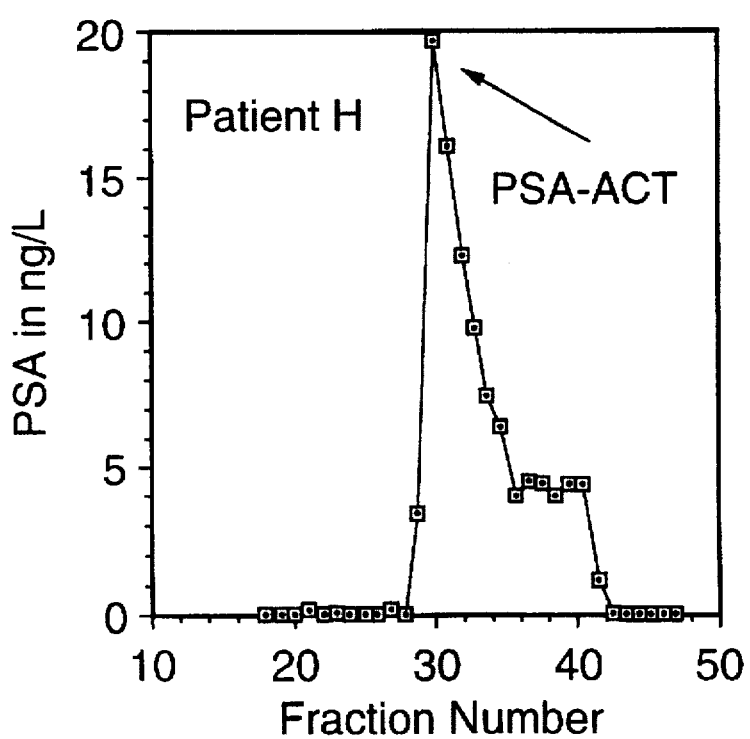
Figure 8C:
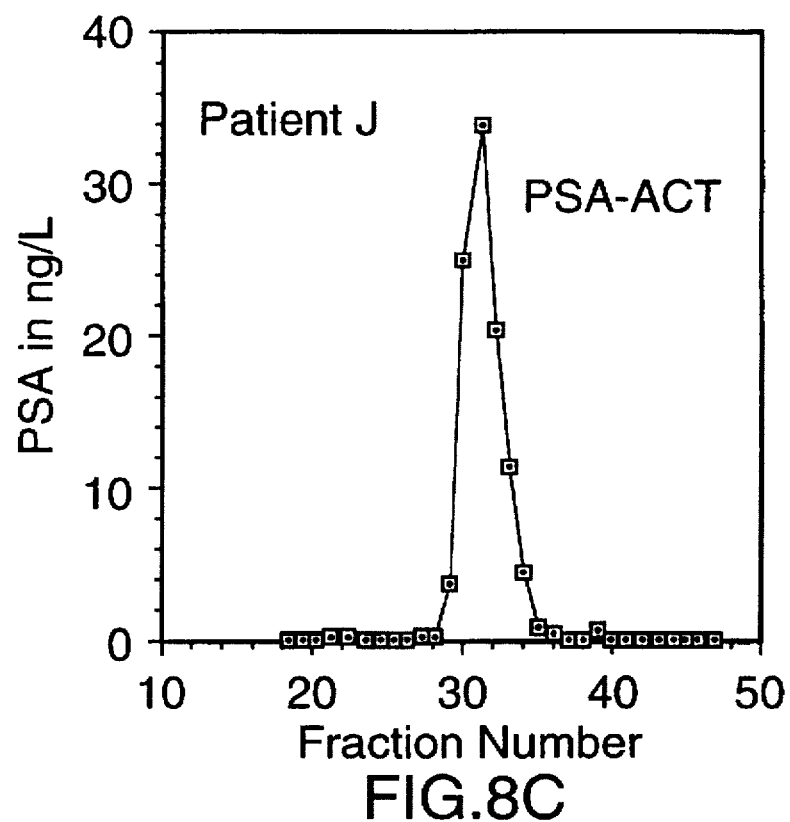
Figure 8D:
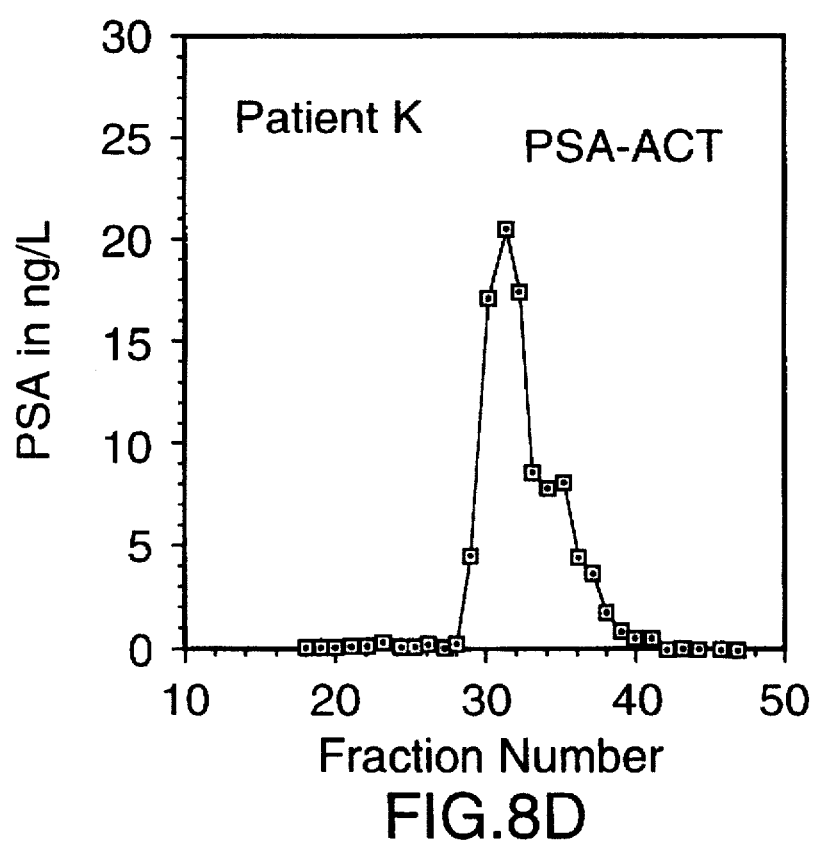
Figure 8E:
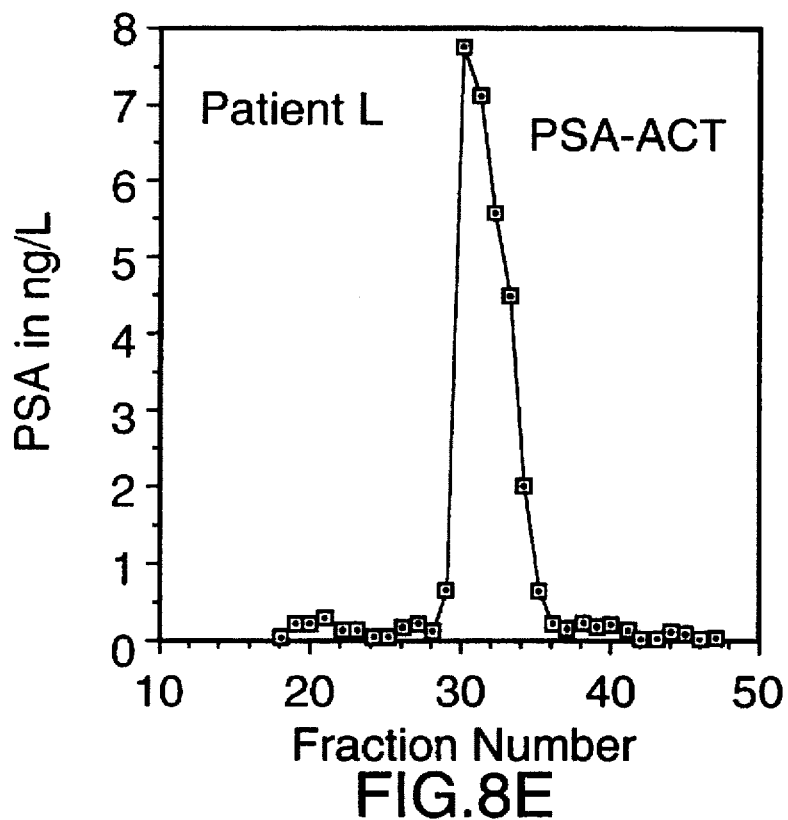
Figure 8F:
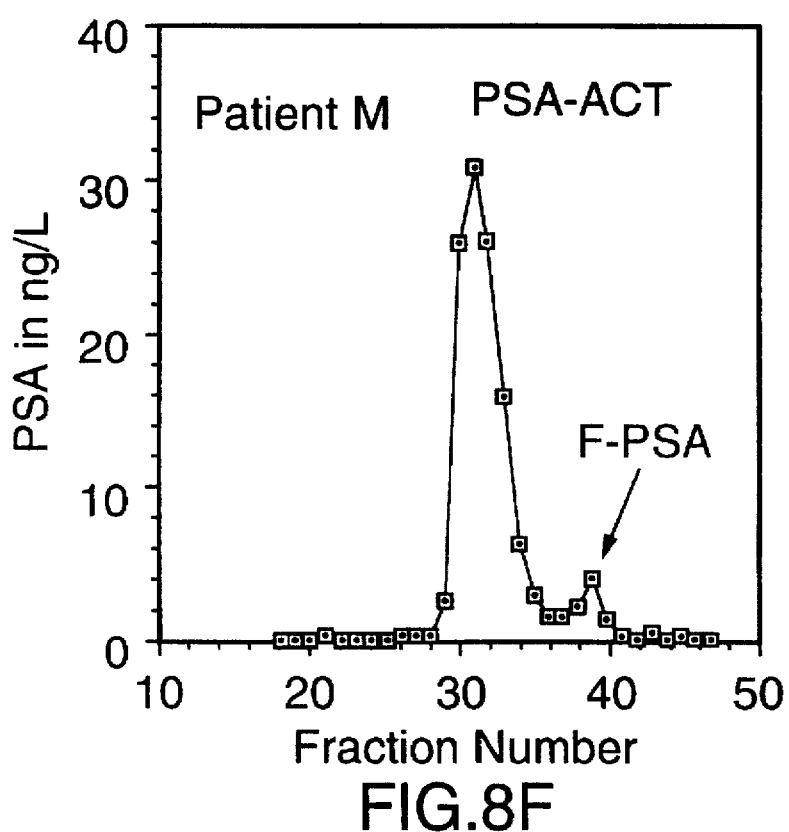

The risk for cancer relapse was significantly lower in patients with PSA-postive tumors than in patients with PSA-negative tumors. The hazard ratio for relapse of PSA-positive patients and PSA-negative patients was 0.32. A similar hazard ratio for overall survival was also observed. Overall and relapse-free survival curves are shown in FIG. 6. The probabilities of relapse-free and overall survivals were substantially higher in the PSA-positive patients than in the PSA-negative ones. FIG. 6 demonstrates that PSA-positive patients relapse less frequently and live longer than PSA-negative patients and that this difference is statistcally significant (P =0.06 and 0.04, respectively). Of the 174 patients, 42 had cancer relapse and 27 died. The overall follow-up time for these patients ranged between 7 and 67 months with a median of 33 months. PSA immunoreactivity higher than 0.03 ng/mg was detected in 27% of the patients (47/174). Without considering the follow-up time PSA-positive patients were less likely to relapse or die than PSA-negative patients (11% of PSA-positive patients versus 29% of PSA-negative patients for cancer relapse and 6% of PSA-positive patients versus 19% of PSA negative patients for death).

The data shows that breast tumors produce PSA, an antigen that was originally thought to be highly specific for the prostate. Previous immunohistochemical studies found no PSA immunoreactivity in breast or other tumors (17) or found occasional PSA immunoreactivity with polyclonal but not monoclonal antibodies, suggesting cross-reactivity effects (18).

The percentage of tumors producing PSA is significant (approximately 29%) similar or higher to the percentage of tumors with amplification of the HER-2 oncogene (19). The PSA form in the tumor has a molecular weight of approximately 30 Kda and corresponds to the free PSA molecule.

Figure 5:
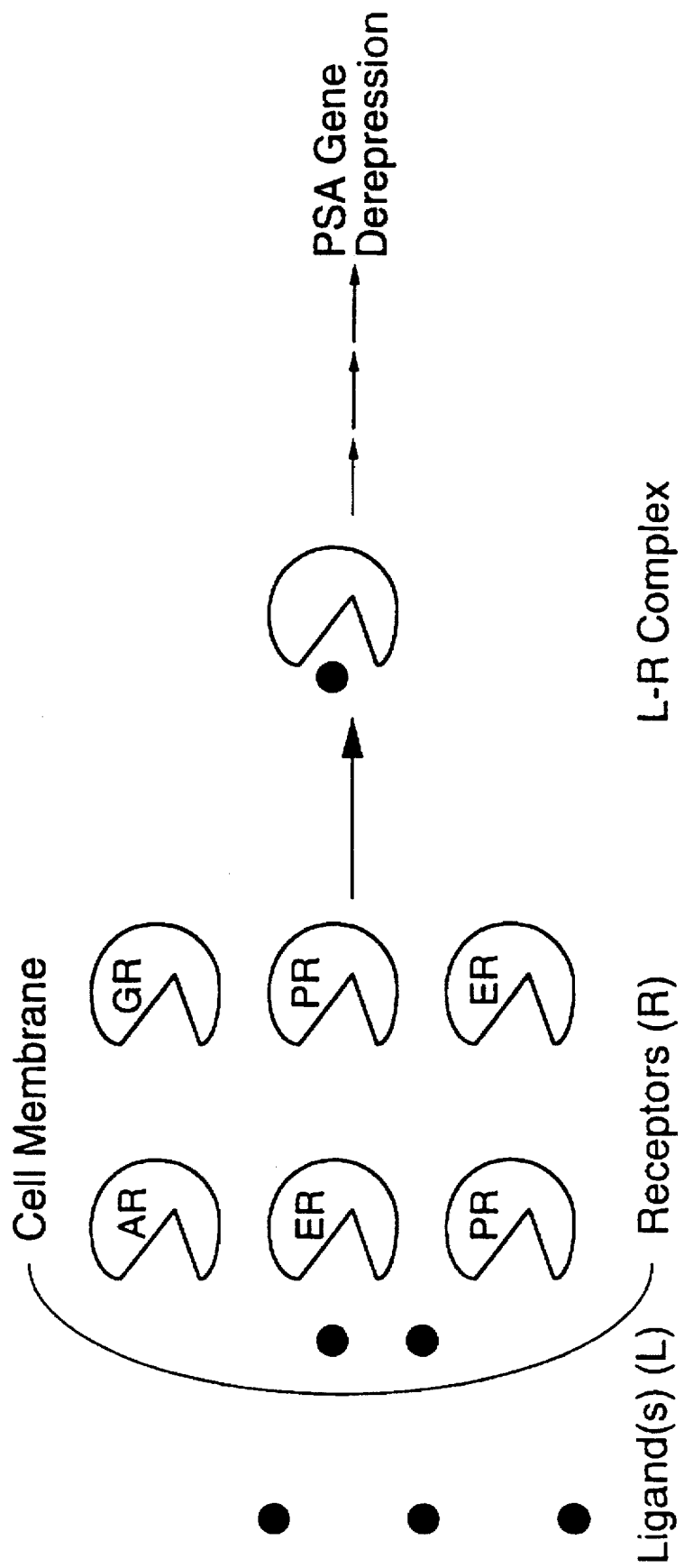
FIG. 5. Proposed scheme for PSA production by breast tumors. Circulating ligands associate with either estrogen, progesterone, androgen or glucocorticoid receptors. The complexes formed act to regulate the PSA gene. Receptor-negative tumors cannot induce PSA production. The subgroup of tumors which are receptor-positive but do not produce PSA are either deficient in ligands, possess defective receptors or they have a defect downstream from the L-R complex. Upregulation of the PSA gene is mediated by AR, PR but not ER.

The production of PSA by breast tumors is due to PSA gene upregulation by steroid hormone receptors bound to either progestins, androgens or glucocorticoids (FIG. 5). This is indicated by the finding that most tumors producing PSA are steroid hormone receptor-positive. From the 151 PSA-positive tumors, only 20 were negative for estrogen and/or progesterone receptors. From these, fifteen had detectable estrogen and/or progesterone receptor levels but their concentration was below the cutoff point of 10 fmol/mg of protein. Only five PSA-positive tumors (3.3%) had undetectable estrogen and progesterone receptor levels by the method used. In these five tumors the PSA immunoreactivity of the extracts was relatively low (0.05, 0.06, 0.14, 0.17 and 0.37 µg/L).

Recent reports suggest that PSA expression in the prostate may be under the direct influence of hormones, namely synthetic androgens or testosterone (20–23). Our observation that the presence of PSA in breast minors is dependent upon the presence of the steroid hormone receptors and that there is no correlation between levels of PSA and receptors, indicate that the receptors are necessary but not sufficient for PSA production. In addition, one or more as yet unidentified ligands interact with the steroid hormone receptors to form a complex that regulates PSA gene derepression (FIG. 5). Active ligand-receptor complexes apparently exist in only 32% of the steroid hormone receptor-positive tumors. It is not clear if in the rest of the steroid hormone receptor-positive tumors the ligand(s) is/are absent, the receptors are defective as previously suggested (24) or the ligand-receptor complexes are formed but are somehow ineffective at the level of gene derepression.

This mechanism for PSA gene derepression in breast cancer is further supported by the finding that PSA production is associated with younger patient age (P=0.012, Table 3). In patients over the age of 55, only 24% of tumors produce PSA even if the estrogen or progesterone receptor-positive tumors are over 80% of the total. In patients under the age of 35, 33% of tumors produce PSA even if the estrogen and/or progesterone receptor-positive tumors are only 50% of the total. To further demonstrate the effect of age on PSA production the percentage of tumors that produce PSA from the total number of estrogen or progesterone receptor-positive tumors was calculated. These values are 67% (6/9) and 75% (6/8), respectively, for the age group <35 years and 29.7% (80/269) and 38.1% (30/210), respectively, for the age group >55 years (data from Table 3). The higher PSA positivity rate among younger patients may be related to production of the putative ligands of FIG. 5 by the functioning ovaries.

Although disease stage was available only for 203 patients, the association analysis between PSA production and disease stage demonstrates (Table IV and FIG. 4) that there is a clear trend for PSA-positive tumors to be preferentially associated with lower disease stage. The P values did not fall below 0.05 because of the relatively small number of samples in some patient groups.

A practical implication of these findings is that the PSA gene regulation mechanism may be used for treatment of breast tumors. An examination of the ligands involved in steroid hormone receptor binding and PSA gene regulation in breast cancer may assist in this treatment. Breast tumors producing PSA constitute a sizable group (29% of patients) which may be examined in retrospective or prospective studies to establish if patients have a different prognosis or favourable response to selected therapy.

The data indicates that PSA is a favourable prognostic indicator because it is associated more strongly with tumors that are positive for both receptors, with lower disease stage and with improved patient survival (FIG. 6). In the breast tumor, PSA is present in the predominantly free 30–33 kDa form. The suggested mode of PSA production (FIG. 5) based on the findings that the overwhelming majority of PSA-positive tumors have detectable receptors (146/151 or 97%) and that younger patients are more positive than older patients, lead to the conclusion that the PSA-positive tumor is a subgroup that possesses "effective" receptors, capable of gene regulation, as exemplified by PSA production. Then PSA-positive tumor patients will be most likely to respond to steroid hormone therapy. This was recently suggested for the steroid hormone receptor-inducible pS$_2$-BCEI protein, another potential prognostic indicator in breast cancer (25, 26).

A significant proportion of breast tumors (29%) produce PSA. PSA production is associated with steroid hormone receptor-positive tumors, younger age and earlier disease stage. PSA can be used as a routine prognostic marker for breast carcinoma and may play a role in disease initiation and progression. The invention's time-resolved fluoroimmunoassay is sensitive enough to detect levels of PSA as low as 0.05 ug/L in breast tumor extracts which equivalent to approximately 0.03 ng of PSA per mg of total protein.

Serum PSA Subfractions

Previously we had suggested that total serum PSA had no diagnostic or monitoring value. We however, have now discovered that the free 30–33 kDa form of PSA is specifically related to breast cancer and that this free form of PSA could be quantitated in serum to provide a non-invasive in vitro method to diagnose breast and other cancers.

To test this hypothesis male sera, sera from women with breast cancer, and sera from women with breast cancer post-operatively were studied. All types of serum samples with the exception of male sera, were selected on the basis of their total PSA level ($\geq 16$ ng/L), and the availability of sufficient sample volume (>100 uL) for HPLC analysis (Table 7). In general, they approximately represented samples from the upper pentile of their respective serum type.

Separation of serum immunoreactive PSA was done by HPLC followed by immunofluorometric analysis of their corresponding fractions. HPLC was used because it is currently the most sensitive method by which to separate the PSA species, however it is understood that any other method developed for these purposes could also be used. In addition, the detection of the PSA present in the fractions can also be done using several different assays such as enzyme immunoassay, radioimmunoassay, chemi or bio-luminescent immunoassay and fluorogenic immunoassay.

It is also understood by those skilled in the art that PSA subfractions can also be assessed using other techniques including the direct measurement of free PSA and/or PSA-ACT complexes using immunoassays without the need for HPLC or other separation of serum fractions. Such assays utilize specific monoclonal antibodies produced against PSA and have been described in the literature (16). These assays are the preferred mode for determining the relative mount of free and complexed PSA to indicate the presence or absence of breast cancer.

The results revealed for three normal female sera, that the molecular form of immunoreactive PSA is the complexed form; PSA bound to ACT (PSA-ACT; ~100 KDa), which peaks at fraction 30±1 (FIG. 7; panels A,B,C). Free PSA was not detectable (see below). Immunofluorometric analysis of serum fractions from three preoperative females with primary breast cancer demonstrated that the predominant molecular form of PSA is free PSA (F-PSA; ~33 KDa), which peaks at fraction 39±1 (FIG. 7; panels D,E,F). PSA-ACT complex constitutes a minor molecular form in the presurgical serum of the three females with breast cancer. Fractions from seven postsurgical sera were also analyzed in the same manner PSA (FIG. 8). Our results show that the predominant molecular form of PSA in the 6 out of 7 postoperative sera, exists as a complex with ACT. The present clinical status for cases G and H of Table 7 is unknown, but all other subjects are in remission for the times indicated. The predominant molecular form of PSA for case G is F-PSA.

Figure 9A:
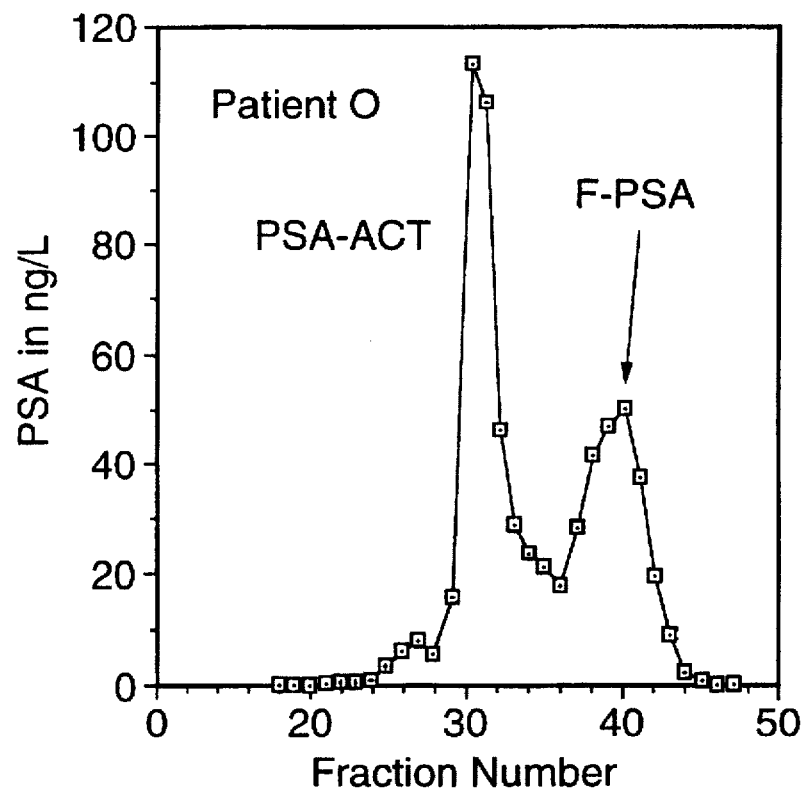
FIG. 9A. Separation of a normal male serum total PSA by high-performance liquid chromatography and assay of the fractions with a highly sensitive time-resolved immunofluorometric methodology. The patient is described in Table 7. The PSA-$\alpha_1$-antichymotrypsin complex (PSA-ACT) elutes at fraction 30±1 (molecular weight of ~100 KDa), and the free PSA (F-PSA) elutes at fraction 39±1 (molecular weight of ~33 KDa). For all sera from male patients, the predominant molecular form in circulation is PSA-ACT.
Figure 9B:
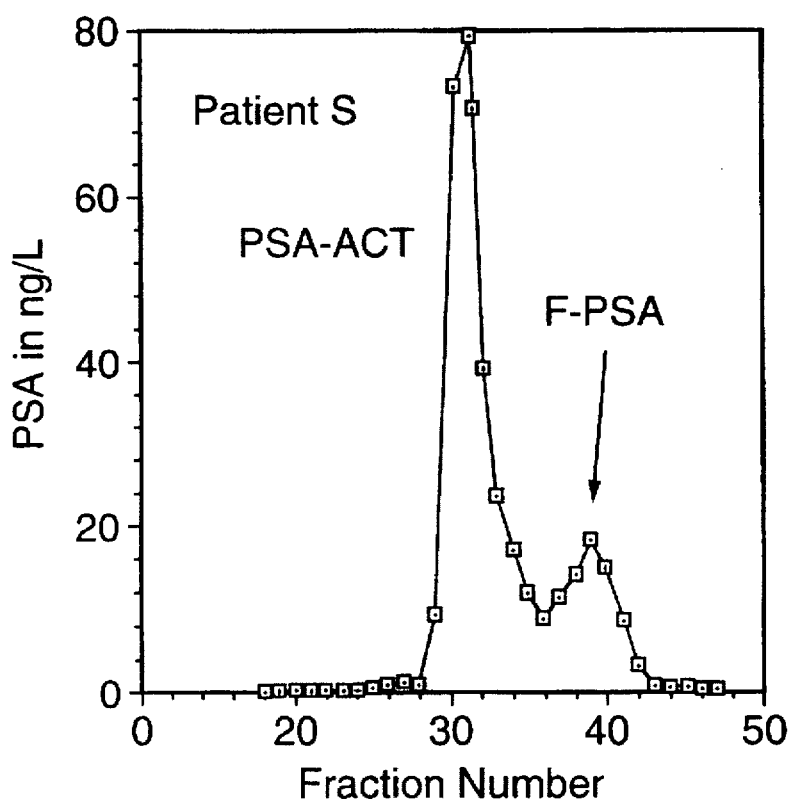
FIG. 9B. Separation of a prostate cancer patient post-radical prostatectomy serum total PSA by high-performance liquid chromatography and assay of the fractions with a highly sensitive time-resolved immunofluorometric methodology. The patient is described in Table 7. The PSA-$\alpha_1$-antichymotrypsin complex (PSA-ACT) elutes at fraction 30+1 (molecular weight of ~100 KDa), and the free PSA (F-PSA) elutes at fraction 39±1 (molecular weight of ~33 KDa). For all sera from male patients, the predominant molecular form in circulation is PSA-ACT.

Immunofluorometric PSA determination of serum fractions from three normal male sera and three sera from post-radical prostatectomized subjects with prostate cancer indicated that the major PSA species in all of these serum samples is the PSA-ACT complex. Representative data are shown in FIG. 9. F-PSA is the minor molecular form of PSA in these sera.

It is known that PSA is primarily produced and secreted by the columnar epithelial cells of the prostate (11, 38). Briefly, PSA is translated as a 261 amine acid preproPSA precursor. It enters the secretory pathway when the signal peptide represented by the pre-region (17 residues) is removed in the endoplasmic reticulum. The resulting inactive proPSA (zymogen) is exocytosed into the lumina of the prostate ducts. The release of seven N-terminal residues results into the 237-amine acid mature extracellular form, enzymatically active PSA. The protease(s) responsible for the formation of the active PSA via proPSA cleavage has not been identified yet. The primary biologic role of PSA is to increase sperm motility via the cleavage of the major seminal gel forming proteins semenogelin I, II, and fibronectin in seminal fluid (SF) into small peptides. Although the majority of the PSA in SF is enzymatically active, about 20–30% is inactive primarily due to clipping between residues 145–146 (lysine-lysine) (49). The nicked PSA remains connected by the internal disulfide bonds, but does not complex to any pretense inhibitors.

The predominant form of immunoreactive PSA in the male serum is the one complexed to ACT (15, 49). Our results confirm that the minor PSA species is indeed F-PSA in normal male serum and serum of post-radical prostatectomy prostate cancer patients (FIG. 9). The F-PSA in serum has not been fully characterized. The uncomplexed and enzymatically inactive PSA could be either the internally clipped PSA or the 244 amine acid proform (zymogen) or even KLK2, a kallikrein highly homologous to PSA. Although PSA may possibly be autocatalytic, the cleavage sites observed are highly suggestive of a trypsin like enzyme. A speculation has been made that this trypsin-like activity and hence the inactivation of PSA by nicking may be attributable to KLK2 (54). However, it seems that this inactivation occurs before PSA is released into the circulation, since the huge excess of protease inhibitors in the blood would have likely complexed with the otherwise non-clipped enzymatically active PSA.

The molecular characterization of immunoreactive PSA in cytosolic breast tumor extracts and normal breast tissue has shown that the predominant molecular form is the F-PSA (40, 43). However, the presence of an enzymatic activity or the determination of its physicochemical and biomolecular properties have not been examined in breast as yet, mostly due to the production and presence of minute amounts in comparison to those of the prostate gland. We have previously demonstrated that fewer than 5% of women have serum PSA concentrations of $\geq 50$ ng/L (50). A recent study involving the measurement of PSA with an optimized ultrasensitive assay (biological detection limit of 1 ng/L) (53) from sera of 212 normal women, revealed that 32% of the women had PSA values of $\leq 1$ ng/L while the median was 2 ng/L. We have previously reported, in a study examining female serum total PSA levels, that there is no association of breast tumor PSA levels with serum PSA either pre or post operatively, and also no substantial difference of serum PSA levels between normal women and women with breast cancer (17). The results of the present study indicate that the predominant and quite possibly the only molecular form of circulating PSA existing in the serum of normal women is PSA complexed with ACT (FIG. 7). Moreover, the predominant molecular form of PSA in the pre-surgical serum of women with breast cancer is the F-PSA; presumably the internally clipped and non-enzymatically active form of PSA the proPSA molecule or KLK2. The results indicate that the female serum presents differences with respect to the presence of PSA molecular form variants between normal and breast cancer afflicted subjects. Determination of the PSA molecular forms in seven post-operative sera from women with breast cancer, indicated with one exception, which we speculate to be a relapsed case, that the major PSA molecular form is the PSA-ACT complex. The degree of post translational modification with reference to PSA clipping could be a distinguisable feature for the diagnosis and monitoring of breast cancer.

Figure 10:
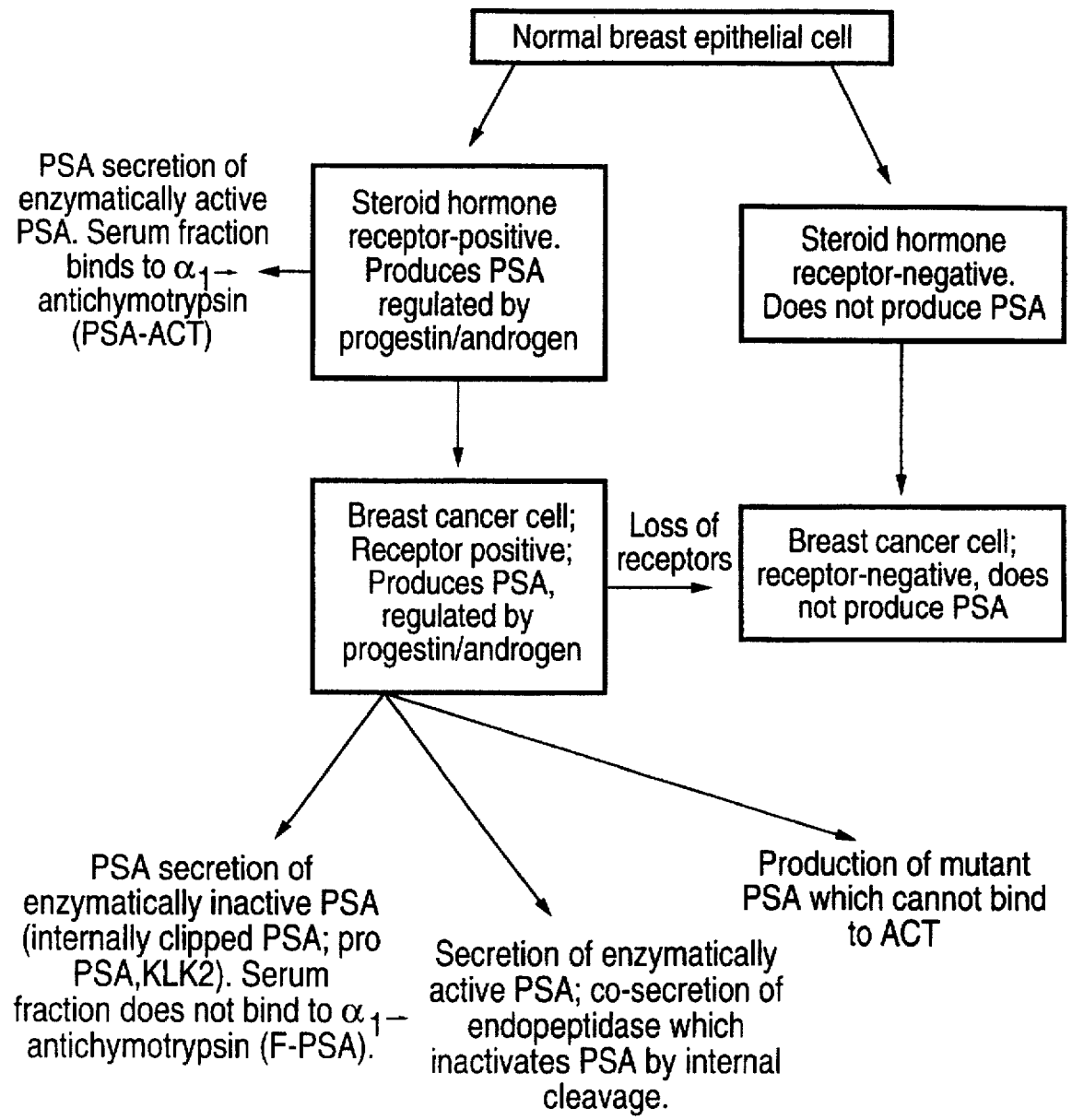
FIG. 10. PSA is produced by steroid hormone receptor-positive breast epithelial cells under regulation by progestins/androgens. Normal epithelial cells produce and secrete enzymatically active PSA which binds to $\alpha_1$-antichymotrypsin when it enters the general circulation. Breast minors seem to produce and secrete enzymatically inactive PSA (either internally clipped PSA, pro PSA or KLK-2) which cannot bind to $\alpha_1$-antichymotrypsin when it enters the general circulation.

The data presented here allow us to propose a simple diagram coveting PSA production by breast epithelial cells (FIG. 10). We suggest that normal breast epithelial cells secrete enzymatically active PSA which binds to $\alpha_1$-antichymotrypsin when it enters the general circulation. Breast cancer cells seem to produce enzymatically inactive PSA which does not bind to ACT and circulates as a free 33 KDa protein. Free PSA may represent internally clipped PSA, pro PSA, KLK-2 or even mutant PSA produced by the tumor. Alternatively, the tumor may produce an endopeptidase which cleaves enzymatically active PSA. The consequences of the loss of enzymatically active PSA from the breast are not known, nor it is known if this loss occurs before or after the malignant transformation.

To summarize, we have examined the molecular forms of PSA in the serum of normal women and women with breast cancer. The results indicate that the molecular forms of PSA differ in females with or without breast cancer. The clinical value of PSA molecular forms was also examined by other investigators for males (57). Determination of the proportions of F-PSA and PSA-ACT may assist in the discrimination of prostate cancer and benign prostatic hyperplasia (BPH) as well as other endocrine cancers. The prospect of measuring PSA molecular forms in the female serum appears clinically useful for the diagnosis and management of breast cancer. Furthermore, measuring active and inactive free forms of PSA may also provide to be useful for the diagnosis of cancers.

METHODS

Patients—Breast Tumors

Approximately 500 breast tumor extracts were, analyzed for steroid hormone receptors, for the p53 tumor suppressor gene product and for PSA, using the invention's new, highly sensitive immunofluorometric procedure.

All primary tumors used in this study were collected from about ten different hospitals in Ontario. Primary breast tumor tissue was immediately stored in liquid nitrogen after surgical resection, transported to the laboratory and stored subsequently at –70° C. until extraction was performed (~1–2 weeks). Approximately 0.5 g of tumor tissue was weighed out, smashed with a hammer if necessary, and pulverized in a Thermovac tissue pulverizer with liquid $N_2$. The resulting powder was transferred into 50 mL plastic tubes along with 10 mL of extraction buffer (0.01 mol/L Tris, 1.5 mmol/L ethylenediaminetetraacetic acid, 5 mmol/L sodium molybdate, pH adjusted to 7.40 with 5 mol/L HCl). The tissue powder was homogenized on ice with a single 5s burst of a Polytron homogenizer. The particulate material was pelleted by 1 h centrifugation at 105,000 g. The intermediate layer (cytosol extract) was collected without disturbing the lipid or particulate layers. Protein concentration of the cytosol extract was determined by the Lowry method and the extracts were stored at –70° C. until analysis (up to three weeks). In determining the total protein of tumor tissue sample to be tested, the protein concentration of the extract may provide the basis for such determination. Hence, the detection level of 0.03 ng of PSA per mg of total protein is determinative for deciding PSA (+ve) or (–ve). Stability studies have revealed that the p53 protein and PSA in the cytosol extracts are stable for at least four months at –70° C.

Estrogen and Progesterone Receptors

Quantitative analysis of estrogen and progesterone receptors (ER, PR) was measured using the Abbott enzyme immunoassay kits (Abbott Laboratories, North Chicago, Ill. 60064). The kits were used according to the manufacturer's instructions.

PSA and p53 Measurement

Analysis of PSA and p53 was performed using the invention's time-resolved fluoroimmunoassay.

Instrumentation

For measuring liquid-phase $Tb^{3+}$ fluorescence in white microtiter wells, we used the CyberFluor 615® Immunoanalyzer, a time-resolved fluorometer. The time-gate settings of the instrument and the interference filter in the emission pathway were the same as described elsewhere (32,33).

PSA MEASUREMENT

Reagents and Solutions

All reagents were purchased from Sigma unless otherwise stated. The coating solution was a 50 mmol/L Tris buffer, pH 7.80, containing 0.5 g of sodium azide per liter. The wash solution was a 5 mmol/L Tris buffer, pH 7.80, containing 0.15 mol of NaCl and 0.5 g of polyoxyethylenesorbitan monolaurate (Tween 20) per liter. The substrate buffer was a 0.1 mol/L Tris buffer, pH 9.1, containing 0.15 mol of NaCl, mmol $MgCl_2$ and 0.5 G of sodium azide per liter. The substrate stock solution is a 10 mmol/L diflunisal phosphate (DFP) solution in 0.1 mol/L NaOH. It is available from CyberFluor Inc., Toronto, Canada. The developing solution contains 1 mol Tris base, 0.4 mol NaOH, 2 mmol, $TbCl_3$ and 3 mmol of EDTA per liter (no pH adjustment). This solution is prepared as described previously (23, 24) and is commercially available by CyberFluor. The assay buffer is a 50 mmol/L Tris buffer, pH 7.80, containing 60 g of BSA, 0.5 mol of KCl, 0.5 g of sodium azide, 50 mL of normal mouse serum and 5 g of Triton X-100 per liter. The polyclonal biotinylated detection antibody and SA-ALP diluent is a 50 mmol/L Tris buffer, pH 7.80, containing 60 g of BSA per liter. The GARIg-ALP conjugate diluent is the same as the polyclonal biotinylated detection antibody diluent but also contains 4% (v/v) of goat serum. The blocking solution was a 50 mmol/L Tris buffer, pH 7.80, containing 10 g of BSA per liter.

Antibodies

The mouse monoclonal MBP0405 and the rabbit polyclonal PBG0101 anti-PSA antibodies were purchased from Medix Biotech, Foster City, Calif. 94404. The SA-ALP conjugate was purchased from Jackson ImmunoResearch, West Grove, Pa. 19390. The alkaline phosphatase-conjugated affinity purified goat anti-rabbit IgG, Fc fragment specific (GARIg-ALP) was also purchased from Jackson. A polyclonal rabbit antibody against $\alpha_1$-antichymotrypsin was purchased from Dakopatts (Glostrup, Denmark).

Standards

Because of the unavailability of a universally accepted standard from PSA, for our studies we used PSA standards in a 50 mmol/L Tris buffer, pH 7.80, containing 6% (w/v) of BSA. A stock PSA solution, prepared from PSA purified from human seminal plasma, was purchased from Scripps Laboratories, San Diego, Calif. 92121. Our final standard solutions were calibrated against standards fro the Hybritech Tandem-PSA kit (Hybritech Inc., San Diego, Calif. 92126). For routine use we recommend six PSA standards with concentrations of 0, 0.025, 0.1, 0.5, 2 and 10 µg/L. These are stable for at least one month at 4° C.

Biotinylation of the Polyclonal Anti-PSA Antibody

The polyclonal anti-PSA antibody, purified by ion-exchange chromatography, was dialyzed overnight against five liters of a 0.1 mol/L sodium biocarbonate solution. This stock solution (~2 mg/ml) was diluted 2-fold with a 0.5 mol/L carbonate buffer, pH 9.1. To this solution we added 1 mg of NHS-LC-Biotin (from Pierce Chemical Co., Rockford, Ill.) dissolved in 50 µL of dimethylsulfoxide, under continuous stirring and incubated for 2 h at room temperature. This biotinylated antibody was used without further purification and stored at 4° C. for at least six months.

Coating of Microtiter Wells

White, opaque 12-well microtiter polystyrene strips were obtained from Dynatech Laboratories, Alexandria, Va. 22314. The wells were coated overnight at room temperature with 500 ng/100 µL/well of coating monoclonal anti-PSA antibody in the coating buffer. Before use, the wells were washed x 2 and blocked for 1 hour with 200 µL/well of the blocking solution.

Assay Procedure

Wash the strips x 6. In each well pipet 50 µL of tumor tissue extract or PSA standards and add 50 µL of assay buffer per well. Incubate for 3 h at room temperature with continuous mechanical shaking and wash x 6. Add 100 µL per well of the biotinylated polyclonal rabbit detection antibody diluted 1,000-fold in the polyclonal detection antibody diluent (100 ng of antibody per well). Incubate for 1 h as above and wash x 6. Add 100 µL per well of SA-ALP conjugate diluted 30,000-fold in the SA-ALP diluent (3 ng of conjugate per well). Incubate for 15 min as above and wash x 6. Add 200 µL/well of the DFP substrate diluted 10-fold just before use in the substrate buffer (working DFP substrate solution is 1 mmol/L) and incubate for 10 min at room temperature with shaking. Add 100 µL/well of the developing solution, mix by shaking for 1 min and read the $Tb^{3+}$ specific fluorescence with the CyberFluor 614 Immunoanalyzer. Data reduction is automatic.

Assay of the PSA-$\alpha_1$-Antichymotrypsin Complex (PSA-ACT)

This assay is exactly the same as the PSA assay described above but instead of using the biotinylated polyclonal rabbit anti-PSA antibody, we used the polyclonal rabbit $\alpha_1$-antichymotrypsin antibody, diluted 500-fold in the SA-ALP conjugate diluent. We then added 100 µL of a 5,000-fold diluted FARIg-ALP conjugate (20 ng per well) and incubated for 30 min with shaking. After washing x 6, we completed the assay by adding the DFP substrate as described in the PSA assay. No effort was made to calibrate this assay because of the unavailability of standard PSA-ACT complex.

PSA was also measured in selected tumor extracts with commercially available kits (a). The Hybritech Tandem®-R PSA kit (Hybritech Inc, San Diego, Calif. 92126), (b). The IRMA-Count® PSA kit (Diagnostic Products Corp., Los Angeles, Calif. 90045) and (c). The Abbott $IM_x$® automated PSA method (Abbott Laboratories, Chicago, Ill., U.S.A.). High performance liquid chromatography was performed with a Shimadzu system with an absorbance monitor at 280 nm (Shimadzu Corp., Kyoto, Japan), isocratically, using a mobile phase of 0.1 mol/L $NaH_2SO_4$—0.1 mol/L $NaH_2PO_4$, pH 6.80. Flow rate was 0.5 mL/min. The gel filtration column used was a Bio-Sil SEC-400, 600 mm×7.5 mm (BioRad Labs, Richmond, Calif.). The column was calibrated with a molecular weight standard solution from BioRad, containing thyroglobulin (670 KD), IgG (158 KD) ovalbumin (44 KD), myoglobin (17 KD) and cyanocobalamin (1.4 KD). Fractions of 0.5 mL each were collected with a fraction collector, Model FRAC-100 (Pharmacia, Uppsala, Sweden) after injecting a 150 mL sample.

Statistical Analysis

The chi-square ($X_2$) test was used to determine the statistical significance of differences in distributions and all chi-square values and the corresponding P values were calculated by the statistical software SAS (SAS Institute Inc., Cary, N.C., USA).

p53 Measurement

Solutions and Reagents

Lysis buffer: 150 mM CaCl, 20 mM Tris, 1% Nonidet P-40. 0.5 mM phenylmethysulfonylchloride (PMSF). 1 µg ml$^{-1}$ leupeptin. 50 g ml$^{-1}$ aprotinin. Sample diluent (diluent for cell lysates, serum, polyclonal anti-p$^{53}$ rabbit antiserum and alkaline phosphatase-conjugated goat anti-rabbit antibody): 50 mM Tris, pH 7.40, containing 60 g bovine serum albumin (BSA) and 1 g sodium azide per liter. Monoclonal anti-p$^{53}$ antibody diluent; 50 mM Tris, pH 7.40, containing 60 g bovine serum albumin, 1 g sodium azide and 0.5 mol KCl per liter.

Substrate buffer 0.1M Tris, pH 9.1, 0.15M NaCl, 1 mM MgCl. Developing solution: $2\times10^{-5}$, TbCl$_3$, $3\times10^{-3}$ EDTA. 0.4M NaOH, 1M Tris base (no Ph adjustments). Prepare as described elsewhere (32). Wash solution: Distilled water. Coating buffer: 50 mM Tris, pH 7.80, containing 1 g of sodium azide per liter. The phosphate ester of 5-fluorosalicylic acid (FSAP) was obtained from Cyber-Fluor Inc., Toronto, Canada. It is stored as a 10 mM stock solution in 0.1 M NaOH at 4° C. for many months. This stock is diluted 10-fold in the substrate buffer just before use. All other chemicals were from Sigma Chemical Co., St. Louis, Mo., USA, except Nonidet P-40 (Boehringer-Mannheim, Indianapolis, Ind., USA) TbCl$_3$.6H$_2$O IGFS Chemicals, Columbus, Ohio, USA) and the biotinylation reagent NHS-LC-Biotin (Pierce Chemical Co., Rockford, Ill., USA).

p53 Standards

Recombinant mutant human p53 protein standards in the range from 0.25–4 ng ml$^{-1}$ were obtained from Oncogene Science, Inc., Uniondale, N.Y., USA and were considered the primary standards. These standards were used to optimize the assay and standardize cell lysates for subsequent studies. Another human wild-type recombinant p53 solution, prepared as described elsewhere (33) was a gift to us by Dr. C. Prives, Columbia University. This p53 preparation was diluted in the sample diluent to make standard solutions.

Antibodies

The mouse anti-p53 monoclonal antibodies, PAb 421 and PAB 240 were kindly provided by Dr. S. Behchimol, Ontario Cancer Institute. These are tissue culture supernatants containing approximately 30 µg ml$^{-1}$ antibody. The rabbit polyclonal anti-p53 antibody, CM-1, was obtained from Dimension Labs, Mississauga, Ontario, Canada. The goat anti-rabbit antibody, conjugated to alkaline phosphatase and the goat anti-mouse antibody, F$_c$ specific, both approximately 1 mg ml$^{-1}$, were obtained from Jackson Immunoresearch, West Grove, Pa., USA.

Immunoassay of p53

White, opaque, 12-well microtiter strips (Dynatech Labs, Alexandria, Calif.<USA) were coated with a goat anti-mouse antibody by pipetting 100 µl 500 ng well$^{-1}$ of the antibody solution in the coating buffer. After overnight incubation at room temperature, the wells were washed four times with distilled water. The wells were then blocked by pipetting 200 µl well of the sample diluent, incubating for 1 h and washing as above. The wells were then used for the assay as follows. We add 100 ng well$^{-1}$ of mouse monoclonal anti-pt3 antibody (PAb 421 or PAb 240) and 50 µl of sample (p53 standards of cell lysates). The antibodies are cell culture supernatants containing about 30 µg ml$^{-1}$ of antibody and they were diluted x 20 in the monoclonal anti-p53 antibody diluent. The cell lysates were used in different dilutions in the sample diluent, varying from 10–1000-fold. After 3 h incubation with shaking at 37° C., the plates were washed x 4. We then added 100 µl well$^{-1}$ of the polyclonal rabbit anti-p53 antibody (diluted 5000-fold in the sample diluent) and incubated with shaking for 1 h at room temperature. After washing x 4, we added 100 µl well$^{-1}$ of the goat anti-rabbit alkaline phosphatase conjugate solution (diluted 5000-fold in the sample diluent) and incubated with shaking for 1 h at room temperature. The strips were washed again x 4 and 100 µl well$^{-1}$ of the FSAP solution ($10^{-3}$ M in the substrate buffer were added and incubated for 10 min with shaking at room temperature. The fluorescent complex was then formed by adding 100 µl well$^{-1}$ of the developing solution followed by brief mixing for 1 min. Time-resolved fluorometric measurements at 615 nm were performed on the CyberFluor 615 Immunoanalyzer. Data reduction and plotting of calibration curves was automatic through the analyzer software.

Detection of PSA mRNA

Detection of PSA mRNA can be accomplished by the method of Deguchi et al (34) or a modification of it. This method involves isolation of total RNA or mRNA from tumors, synthesis of cDNA by reverse transcription and PCR amplification of the cDNA using PSA specific primers. The sequence of primers used are as follows:

5'-TCG-GCA-AGT-TCA-CCC-TCA-3'

5'-CCC-TCT-CCT-TAC-TTC-ATC-C-3'.

PCR amplification produces a fragment of 754 base pairs which is electrophoresed on agarose gels and Southern blotted to Hybond N+ membrane. A probe (5'-GGA-ACC-TTG-GAA-ATG-ACC-AG-3') labeled with fluorescein is added to hybridize with cDNA for PSA. The probe is detected using chemiluminescence reagents from Amersham International.

Breast Cancer Survival and ER-negative, PSA-positive Study

One hundred and seventy four patients with primary breast cancer were included in this study. All patients were treated and followed at the Department of Gynecologic Oncology at the University of Turin. Ages of these patients ranged from 25 to 91 years with a median of 56 years. Thirty two percent of the patients were <50 years and 69% >50 years. The follow-up time ranged from 7 to 67 months with a median of 33 months.

Clinical and pathological information, including clinical stage, histological cell type and grade, axillary node involvement, tumor size, presence of ER and PR in tumor cells and adjuvant treatment after surgery, was collected for each patient. According to the TNM staging system, 45%, 47% and 8% of the patients had stage I, II and III or IV, respectively. Each breast cancer specimen was also histologically graded and typed. Thirty nine percent of patients had low grade (I), 42% had moderate grade (II), and 19% had high grade (III). Seventy percent of patients had ductal carcinomas. The rest had lobular (13%), lobular in situ (2%), medullary (5%), papillary (2%), tubular (2%), tubulo-lobular (3%), or unknown types (3%). In the data analysis, histological type was grouped into two categories, i.e. ductal versus non-ductal, because of the small number of patients who had types other than ductal carcinomas.

The size of tumor in these patients ranged from 0.7 to 6 cm, and median and mean sizes were identical, 2.4 cm. Fiftyone percent of the patients had tumor invading the axillary lymph nodes. Of the 174 patients, 56% were treated with adjuvant therapy as follows: tamoxifen (37%), chemotherapy (15%), or both (4%). The rest (44%) received no further treatment after surgery.

Demographic, clinical and pathological variables, including age, clinical stage, histological grade and type, nodal status, tumor size, ER and PR, and adjuvant treatment, were compared between PSA-positive and PSA-negative groups, using the contingency table and Chi-square test in order to examine the associations between PSA and these variables. The relationship between each of the study variables and relapse-free or overall survival was expressed by the hazard ratio and its 95% confidence interval, which was calculated univariately using the Cox proportional hazard regression model (35). The multivariate Cox regression model was also employed to evaluate the impact of PSA immunoreactivity on patient survival while controlling for other clinical and pathological variables which may also affect the survival, such as clinical stage (I, II or III/IV), nodal status (positive or negative), tumor size (greater or less than mean size), steroid hormone receptors (presence or absence), and adjuvant treatment (none, tamoxifen, or both tamoxifen and chemotherapy). Kaplan-Meier relapse-free and overall survival curves (36) were constructed to demonstrate the survival difference between PSA-positive and negative groups. The logrank test (37) was used to examined the significance of the differences between survival curves.

Serum Samples for PSA Subfraction Study

Three presurgical sera with total PSA values $\geq 50$ ng/L were selected from a series of 198 presurgical sera of patients with primary breast cancer. No other criterion was used to select these three sera. A total of seven post-surgical sera with total PSA $\geq 16$ ng/L were selected from another series of 346 breast cancer patients who were treated by surgery. Three normal (from non-breast cancer subjects) sera with total PSA $\geq 35$ ng/L were also selected from a total of 212 sera from female blood donors. These were provided by the Red Cross Blood Transfusion Service in Toronto. Other clinical samples included sera from three normal male blood donors and sera from three males who underwent radical prostatectomy for prostate cancer. All six male sera had PSA $\geq 80$ ng/L. All samples were stored at $-20°$ C.

We selected sera with total PSA $\geq 16$ ng/L in order to be able to determine the PSA molecular forms by HPLC followed by PSA immunofluorometry. Samples with total PSA<16 ng/L are not suitable because the individual HPLC fractions contain very little PSA which is difficult to measure.

High-performance liquid chromatography (HPLC) of the Serum PSA Subfraction Samples HPLC analysis was performed with a Hewlett Packard 1050 system. The mobile phase was a 0.1 mol/L sodium sulphate and 0.1 mol/L sodium dihydrogen phosphate, pH 6.80. The gel filtration column used was a TSK-GEL G3000SW, 60 cm×7.5 mm (TosoHaas, Montgomeryville, Pa. 18936) and was calibrated with a molecular mass standard solution from Bio-Rad (Bio-Rad Laboratories, Hercules, Calif. 94547). The flow rate was 0.5 mL/min and the HPLC was run isocratically. After injection of 100–500 uL of each centrifuged sample, fractions of 0.5 mL were collected and analyzed for PSA using the outlined method below. Sample carry over of <5% was ensured by in between-sample-injection column and injector washings, and by the order of sample injection (e.g. the samples with the highest total PSA were injected last).

PSA Immunoassay of the HPLC Serum Subfraction Samples

PSA determinations were performed using a modified methodology from our highly sensitive and specific immunofluorometric procedure previously established and described in detail elsewhere (18). Briefly, the PSA assay uses a mouse monoclonal anti-PSA capture antibody coated to polystyrene microtiter wells, a biotinylated monoclonal anti-PSA detection antibody, and alkaline phosphatase-labeled streptavidin (SA-ALP). In this immunoassay, 100 uL of sample is incubated with the coating antibody in the presence of 50 uL of assay buffer containing the monoclonal anti-PSA detection antibody. After 1 h incubation followed by washing x 6, the SA-ALP conjugate is added for 15 min., followed by another washing x 6. The activity of ALP is then measured by adding the substrate 5-fluorosalicylphosphate, incubating for 0 min. and then by adding a $Tb^{3+}$ and EDTA-containing developing solution. After 1 min. the fluorescence is measured in the time-resolved fluorometric mode with the Cyberfluor-615 Immunoanalyzer (Cyberfluor Inc., Toronto, Ontario). This assay has a biological detection limit of 1 ng/L of PSA. Details are described elsewhere (18). All assays were run in duplicate.

Although preferred embodiments of the invention are described herein in detail, it will be understood by those skilled in the art that variations may be made thereto without departing from the spirit of the invention or the scope of the appended claims.

TABLE I

Analysis of PSA in Breast Tumor Extracts

| | PSA, mg/L | | | |
|---|---|---|---|---|
| Number of Patients | <0.05 | $\geq 0.05$ | $\geq 0.10$ | $\geq 0.30$ |
| 525 | 374 | 151 | 96 | 49 |
| % of Samples | 71.2% | 28.8% | 18.3% | 9.3% |

TABLE II

Relationship Between Estrogen and Progesterone Receptors, PSA and p53 Levels in Breast Tumor Extracts[1]

| Samples (N = 525) | PSA (+) (%) | PSA (−) (%) | P Value |
|---|---|---|---|
| ER (+) 393 | 127(32.3) | 266(67.7) | |
| ER (−) 132 | 24(18.2) | 108(81.8) | 0.002 |
| PR (+) 321 | 111(34.6) | 210(65.4) | |
| PR (−) 204 | 40(19.6) | 164(80.4) | <0.001 |
| ER (+) or PR (+) 407 | 131(32.2) | 276(67.8) | |
| ER(−) and PR (−) 118 | 20(16.9) | 98(83.1) | 0.001 |
| ER (+) and PR (+) 307 | 107(34.8) | 200(65.2) | |
| ER (+) and PR (−) 86 | 20(23.3) | 66(76.7) | |
| ER (−) and PR (+) 14 | 4(28.6) | 10(71.4) | |
| ER (−) and PR (−) 118 | 20(16.9) | 98(83.1) | 0.002 |

| Samples (N = 558) | p53 (+) (%) | p53 (−) (%) | P Value |
|---|---|---|---|
| ER (+) 416 | 64(15.4) | 352(84.6) | <0.001 |
| ER (−) 142 | 50(35.2) | 92(64.8) | |

TABLE II-continued

Relationship Between Estrogen and Progesterone Receptors, PSA and p53 Levels in Breast Tumor Extracts[1]

| | | | |
|---|---|---|---|
| PR (+) 338 | 47(13.9) | 291(86.1) | <0.001 |
| PR (−) 220 | 67(30.4) | 153(69.6) | |
| ER (+) or PR (+) 428 | 68(15.9) | 360(84.1) | <0.001 |
| ER (−) and PR (−) 130 | 46(35.4) | 84(64.6) | |

| Samples (N = 474) | p53 (+) (%) | p53 (−) (%) | P Value |
|---|---|---|---|
| PSA (+) 90 | 20(22.2) | 70(77.8) | P = 0.37 |
| PSA (−) 384 | 103(26.8) | 281(73.2) | |

[1] For negativity cutoff levels see text. Values in brackets are percentages.

TABLE III

Distribution of PSA-Positive, Estrogen Receptor-Positive and Progesterone Receptor-Positive Tumors in Various Age Groups % of Positive Tumors[1]

| Patient Age (Years) PSA (+) | ER (+) | PR (+) | |
|---|---|---|---|
| <35 N = 18 | 33.3(6/18) | 50.0(9/18) | 44.4(8/18) |
| 35–44 (N = 66) | 36.4(24/66) | 71.2(47/66) | 62.1(41/66) |
| 45–54 (N = 104) | 38.5(40/104) | 64.4(67/104) | 58.7(61/104) |
| >55 (N = 336) | 23.8(80/336) | 80.1(269/336) | 62.5(210/336) |
| P Value[2] | 0.012 | 0.001 | 0.45 |

[1] In brackets are numbers of positive tumors per total number of tumors in each group. N = number of patients per group.
[2] P value for comparing the distribution of positive or negative tumors for each parameter, in the various age groups.

TABLE IV

Association of PSA-Positive Tumors with Disease Stage

| Disease Stage | % of PSA-Positive Tumors[1] |
|---|---|
| 0 | 42.9(6/14) |
| 1 | 30.7(35/114) |
| 2 | 22.0(13/59) |
| 3 | 12.5(2/16) |
| P | 0.18 |
| 0–1 | 32.0(41/128) |
| 2–3 | 20.0(15/75) |
| P | 0.06 |

[1] In brackets are numbers of positive tumors per total number of tumors in each group.

TABLE V

Relationship between PSA Immunoreactivity and ER & PR

| Receptor Status | No. of Patients | No. of PSA + | OR & 95% CI | p value |
|---|---|---|---|---|
| ER−;PR− | 226 | 32(14%) | 1.00 | |
| ER+,PR− | 139 | 28(20%) | 1.53(0.88–2.67) | 0.13 |
| ER−,PR+ | 58 | 24(41%) | 4.28(2.25–8.14) | <0.01 |
| ER+,PR+ | 852 | 302(35%) | 3.33(2.23–4.96) | <0.01 |

OR: Odds ratio.
CI: Confidence interval.

TABLE VI

Associations between PSA and relapse-free survival stratified by the status of estrogen receptors

| ER status | PSA(+) patients ratio | Hazards Interval | 95% confidence value | P |
|---|---|---|---|---|
| ER cutoff at 10 fmol/mg | | | | |
| Univariate analysis | | | | |
| ER(+) (n = 112)[2] | 36 | 0.98 | 0.37–2.61 | 0.97 |
| ER(−) (n = 57) | 9 | 0.16 | 0.02–1.22 | 0.08 |
| Multivariate analysis[3] | | | | |
| ER(+) (n = 112) | 36 | 0.80 | 0.27–2.32 | 0.68 |
| ER(−) (n = 57) | 9 | 0.13 | 0.02–1.15 | 0.07 |
| ER cutoff at 20 fmol/mg | | | | |
| Univariate analysis | | | | |
| ER(+) (n = 95) | 27 | 1.42 | 0.46–4.34 | 0.54 |
| ER(−) (n = 74) | 18 | 0.18 | 0.04–0.76 | 0.02 |
| Multivariate analysis | | | | |
| ER(#) (n = 95) | 27 | 0.96 | 0.27–3.33 | 0.94 |
| ER(−) (n = 74) | 18 | 0.20 | 0.04–0.93 | 0.04 |

[1] The ratio of hazards between PSA-positive and PSA-negative patients.
[2] N = number of patients.
[3] Adjusted for age, clinical stage, nodal status tumor size, and histological grade.

TABLE VII

Clinical samples used in this study

| CASE ID[1] | SERUM TYPE | GENDER | PSA LEVEL in ng/L | TIME OF |
|---|---|---|---|---|
| A | normal; non-breast cancer | female | 36 | Ra |
| B | normal; non-breast cancer | female | 50 | Ra |
| C | normal; non-breast cancer | female | 80 | Ra |
| D | breast cancer; pre-surgical | female | 54 | <1 month |
| E | breast cancer; pre-surgical | female | 59 | <1 month |
| F | breast cancer; pre-surgical | female | 82 | <1 month |
| G[2] | breast cancer; post-surgical | female | 61 | 163 month |
| H | breast cancer; post-surgical | female | 65 | 92 months |
| I | breast cancer; post-surgical | female | 63 | 36 months |
| J | breast cancer; post-surgical | female | 53 | 104 month |
| K | breast cancer; post-surgical | female | 50 | 1 month |
| L | breast cancer; post-surgical | female | 16 | 36 months |
| M | breast cancer; post-surgical | female | 101 | 1 month |
| N | normal; non-prostate cancer | male | 413 | Ra |
| O | normal; non-prostate cancer | male | 554 | Ra |
| P | normal; non-prostate cancer | male | 544 | Ra |
| Q[3] | post-radical prostatectomized | male | 84 | 7 months |
| R | post-radical prostatectomized | male | 132 | 10 months |
| S | post-radical prostatectomized | male | 420 | 21 months | i. The volume injected into the HPLC column was ~500 uL for all samples with the exception of cases D, E, F, and J which were 200 uL, 100 uL, 100 uL, and 460 uL, respectively.
ii. Patients I to M are still in remission. For patients G and H no current clinical status was available.
iii. Patients Q, R, S are still clinically asymptomatic but biochemically relapsed.

REFERENCES

1. Harris, J. R., Lippman, M. E., Veronesi, U., Willett, W. Breast cancer, (first of three parts). New Engl. J. Med., 1992; 327: 319–28.
2. Harris, J. P., Lippman, M. E., Veronesi, U., Willett, W. Breast cancer, (second of three parts). New Engl. J. Med., 1992; 327: 390–8.
3. Harris, J. P., Lippman, M. E., Veronesi, U., Willett, W. Breast cancer, (third of three parts). New Engl. J. Med., 1992; 327: 473–80.
4. McGuire, W. L., Clark, G. M. Prognostic factors and treatment decisions in axillary node-negative breast cancer. New Engl. J. Med., 1992; 326: 1756–61.
5. McGuire, W. L., Tandon, A. K., Craig Alfred, D., Chamness, G. C., Clark, G. M. How to use prognostic factors in axillary node-negative breast cancer patients. J. Natl. Cancer Inst., 1990; 82: 1006–15.
6. Muss, H. B. Endocrine therapy for advanced breast cancer: a review. Breast Cancer Res. Treat., 1992; 21: 15–26.
7. Carter, H. B., Coffey, D. S. The prostate: an increasing medical problem. The Prostate, 1990; 16: 39–48.
8. Nomura, A. M. Y., Kolonel, L. N. Prostate cancer: A current perspective. Am. J. Epidemiol., 1991; 13: 200–27.
9. Bruchovsky, N., Brown, E. M., Coppin, C. M., et al. The endocrinology and treatment of prostate tumor progression. Prog. Clin. Biol. Res., 1987; 239: 347–57.
10. Thompson, T. C. Growth factors and oncogenes in prostate cancer. Cancer Cells, 1990; 2: 345–354.
11. Oesterling, J. E. Prostate specific antigen: a critical assessment of the most useful tumor marker for adenocarcinoma of the prostate. J. Urol., 1991; 145: 907–923.
12. Diamandis, E. P. Immunoassays with time-resolved fluorescence spectroscopy. Principles and applications. Clin. Biochem., 1988; 21: 139–150.
13. He, Y., Diamandis, E. P. Ultrasensitive time-resolved immunofluorometric assay of prostate-specific antigen in serum. Clin. Chem., 1993 (in press).
14. Hassapoglidou, S., Diamandis, E. P., Sutherland, D. J. A. Quantification of p53 protein in tumor cell lines, breast tissue extracts and serum with time-resolved immunofluorometry. Oncogene, 1993 (in press).
15. Stenman, U. H., Leinonen, S., Alfthan, H., Rannikko, S., Tuhkanen, K., Alfthan, O. A complex between prostate-specific antigen and $a_1$-antichymotrypsin is the major form of prostate-specific antigen in serum of patients with prostatic cancer: Assay of the complex improves clinical sensitivity for cancer. Cancer Res., 1991; 51: 222–6.
16. Lilja, H., Christensson, A., Dahlen, U., et al. Prostate-specific antigen in serum occurs predominantly in complex with $a_1$-antichymotrypsin. Clin. Chem., 1991; 37: 1618–25.
17. Ford, T. F., Butcher, D. N., Masters, J. R. W., Parkinson, C. M. Immunocytochemical localisation of prostate-specific antigen specificity and application to clinical practice. British J. Urol., 1985; 57: 50–5.
18. Papotti, M., Paties, C., Peveri, V., Moscuzza, L., Bussolati, G. Immunocytochemical detection of prostate-specific antigen (PSA) in skin adnexal and breast tissues and tumors. Bas. Appl. Histochem., 1989; 33: 25–9.
19. Slamon, D. J., Clark, G. M., Wong, S. C. et al. Human breast cancer: correlation of relapse and survival with amplification of the HER-2/neu oncogene. Science, 1987; 235: 177–82.
20. Wolf, D. A., Schulz, P., Fittler, F. Transcriptional regulation of prostate kallikrein-like gene by androgen. Mol. Endocrinol., 1992; 6:753–62.
21. Henttu, P., Liao, S. S., Vihko, P. Androgens up-regulate the human prostate-specific antigen messenger ribonucleic acid (mRNA) but down-regulate the prostatic acid phosphatase mRNA in the LNCaP cell line, Endocrinology, 1992; 130: 766–72.
22. Montgomery, B. T., Young, C. Y., Bilhartz, D. L., Andrews, P. E., Prescott, J. L., Thompson, N. F. Hormonal regulation of prostate-specific antigen (PSA) glycoprotein in the human prostate adenocarcinoma cell line, LNCaP. Prostate, 1992; 21: 63–73.

23. Weber, J. P., Oesterling, J. E., Peters, C. A., Partin, A. W., Chan, D. W., Walsh, P. C. The influence of reversible androgen deprivation on serum prostate-specific antigen levels in men with benign prostate hyperplasia. J. Urol., 1989; 141: 987–91.

24. Wei, L. L. Transcriptional activation of the estrogen receptor. Clin. Chem., 1993; 39: 341–45.

25. Milgrom, E. The oestrogen-regulated $pS_2$-BCEI protein in breast cancer. In: Goldhirsch, A., ed. Endocrine therapy of breast cancer V. Berlin; Springer Verlag, 1992: 17–22.

26. Foekens, J. A., Rio, M. C., Seguin, P., et al. Prediction of relapse and survival in breast cancer patients by $pS_2$ protein status. Cancer Res., 1990; 50: 3832–7.

27. Rochefort, H. Cathepsin D. in breast cancer. Breast Cancer Res. Treat., 1990; 16: 1–13.

28. Silvestrini, R., Veneroni, S., Benini, E., DiFronzo, G., Daidone, M. G. p53 and cathepsin D are independent of established prognostic factors in breast cancer. Int. J. Oncol. 1992; 1: 507–12.

29. Allred, D. C., et al. Association of p53 Protein Expression with Tumor Cell Proliferation Rate and Clinical Outcome in Node-Negative Breast Cancer. J. Natl. Cancer Inst. 1993; 85: 200–206.

30. Thor, A. D., et al. Accumulation of p53 Tumor Suppressor Gene Protein: An Independent Marker of Prognosis in Breast Cancers. J. Natl Cancer Inst. 1992; 84: 845–855.

31. Henderson, I. C. (1991). In *Breast Diseases*, Harris, J. R., Hellman, S., Henderson, I. C., Kinne, D. (eds). J. P. Lippincott: Philadelphia. pp. 332–346.

32. Christopoulos, T. K. and Diamandis, E. P. (1992) Ana. Chem. 64:342–346.

33. Wang, E. H., Friedman, P. N., and Prices, C (1989) Cell 57:379–392.

34. Deguchi, T. et al. (1993) Cancer Research 53:5350–5354.

35. Cox, D. R. J. R. Star Soc(B) 1972; 34: 187–202.

36. Kaplan, E. L. Meier, P. J. Am. Star. Assoc. 1958; 53: 457–481.

37. Mantel, N. Cancer Chemother Rep 1966; 50: 163–170.

38. Armbruster D. A. Prostate-specific antigen: biochemistry, analytical methods, and clinical application. Clin Chem 1993;39:181–95.

39. Van Krieken J. H. Prostate marker immunoreactivity in salivary gland neoplasms. Am J Surg Pathol 1993;17:410–4.

40. Diamandis E. P., Yu H., Sutherland D. J. A. Detection of prostate specific antigen immunoreactivity in breast minors. Breast Cancer Res Treat 1994;32:301–10.

41. Levesque M., Yu H., D'Costa M, Tadross L., Diamandis E. P. Immunoreactive prostate specific antigen in lung tumors. J Clin Lab Anal 1995;9:375–9.

42. Yu H., Diamandis E. P. Prostate specific antigen in milk of lactating women. Clin Chem 1994;41:54–8.

43. Yu H., Diamandis E. P., Monne M., Croce C. M. Oral contraceptive-induced expression of prostate specific antigen in the female breast. J Biol Chem 1995;270:6615–8.

44. Yu H., and Diamandis E. P. Prostate specific antigen immunoreactivity in amniotic fluid. Clin Chem 1995;41:204–10.

45. Melegos D. N., Yu H., Allen L. C., Diamandis E. P. Prostate specific antigen in amniotic fluid of normal and abnormal pregnancies. Clin Chem (In Press).

46. Monne M., Croce C. M., Yu H., Diamandis E. P. Molecular characterization of prostate specific antigen RNA expressed in breast rumor. Cancer Res 1994;54:6344–7.

47. Yu H., Diamandis E. P., Sutherland D. J. A. Immunoreactive prostate specific antigen levels in female and male breast tumors and its association with steroid hormone receptors and patient age. Clin Biochem 1994;27:75–9.

48. Yu H., Diamandis E. P., Zarghami N., Grass L. Induction of prostate specific antigen production by steroids and tamoxifen in breast cancer cell lines. Breast Cancer Res Treat 1994;32:291–300.

49. Christensson A, Laurell C. B., Lilja H. Enzymatic activity of prostate-specific antigen and its reactions with extracellular serine proteinase inhibitors. Eur J Biochem 1990;194:755–63.

50. Yu H., Diamandis E. P. Measurement of serum prostate specific antigen levels in females and in prostatectomized males with an ultrasensitive immunoassay technique. J Urol 1995;153:1004–8.

51. Yu H., Giai M., Diamandis E. P., Katsaros D. Sutherland D. J. A., Levesque M. A., Roagna R., Ponzone P., Sismondi P. Prostate specific antigen is a new favourable prognostic indicator for women with breast cancer. Cancer Res 1995;55:2104–10.

52. Giai M., Yu H., Roagna R., Ponzone P., Katsaros D., Levesque M. A., Diamandis E. P. Prostate specific antigen in serum of women with breast cancer. Br J Cancer 1995;72:728–31.

53. Ferguson R. A., Yu H., Kalyvas M., Zammit S., Diamandis E. P. Ultrasensitive detection of prostate specific antigen by a new time resolved immunofluorometric assay and the Immulite immunochemiluminescent third generation assay: potential applications in prostate and breast cancers. Clin Chem (In Press, 1995).

54. McCormack R. T., Rittenhouse H. G., Finlay J. A., Sokoloff R. L., Wang T. J., 55. Wolfert R. L., Lilja H., Oesterling J. E. Molecular forms of prostate-specific antigen and the human kallikrein gene family: a new era. Urology 1995;45:729–44.

56. Diamandis E. P., Yu H. New biological functions of prostate-specific antigen? J Clin Endocrinol Metab 1995;80:1515–7.

57. Lilja H., Bjork T, Abrahamsson P.-A., Stenman U. H., Shaw N., Dowell B., Oesterling J. E., Pettersson K., Piironen T., Lovgren T. Improved seperation between normals, benign prostatic hyperplasia (BPH), and carcinoma of the prostate (CAP) by measuring free (F), complexed (C) and total concentrations (T) of prostate specific antigen. J Urol (Suppl) 1994;151:400A.

I claim:

1. A method to aid in the diagnosis of breast cancer in a patient, said method comprising:
determining the amount of free PSA relative to PSA-ACT complexes in a serum sample of a patient; wherein the predominance of free PSA compared to PSA-ACT complexes in the sample indicates the presence of breast cancer in the patient.

2. The method of claim 1, wherein said step of determining is performed by an assay selected from the group consisting of an enzyme immunoassay, radioimmunoassay.

3. The method of claim 2, wherein the step of determining comprises an immunoassay.

4. The method of claim 3, wherein the step of determining utilizes monoclonal antibodies to detect free PSA.

5. The method of claim 2, wherein the step of determining utilizes monoclonal antibodies to detect PSA-ACT complexes.

6. The method of claim 3, wherein the immunoassay comprises an enzymatic time-resolved fluorescence immunoassay.

7. The method of claim 6, wherein said enzymatic amplification comprises enzymatic conversion of diflunisal phosphate into a fluorescent chelator by use of alkaline phosphatase-conjugated streptavidin.

8. The method of claim 3, wherein the step of determining utilizes polyclonal antibodies to detect free PSA.

9. A method to aid in the diagnosis of breast cancer in a female patient, comprising:

performing a separation technique on a serum sample of a female patient containing PSA to establish serum sample subfractions; wherein the separation technique separates free PSA from PSA-ACT complex;

performing an assay on the subfractions which is capable of detecting at least 1 ng/L of PSA; and determining the proportion of PSA-ACT complex compared to free PSA in the serum sample subfractions, the predominance of free PSA indicating the presence of breast cancer in the female patient.

10. The method of claim 9, wherein said separation technique comprises HPLC.

11. The method of claim 9, wherein said assay to detect PSA is selected from the group consisting of an enzyme immunoassay, radioimmunoassay, chemiluminescence assay, bio-luminescent assay, fluorogenic immunoassay and electroimmunoassay.

* * * * *